(12) United States Patent
Harvey et al.

(10) Patent No.: US 9,285,369 B2
(45) Date of Patent: *Mar. 15, 2016

(54) ANTIBODY-BASED ARRAYS FOR DETECTING MULTIPLE SIGNAL TRANSDUCERS IN RARE CIRCULATING CELLS

(71) Applicant: NESTEC S.A., Vevey (CH)

(72) Inventors: Jeanne Harvey, Livermore, CA (US); Sharat Singh, Rancho Santa Fe, CA (US); Phillip Kim, Irvine, CA (US); Xinjun Liu, San Diego, CA (US); Robert Barham, San Marcos, CA (US); Limin Liu, San Diego, CA (US)

(73) Assignee: NESTEC S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/529,029

(22) Filed: Oct. 30, 2014

(65) Prior Publication Data

US 2015/0051107 A1 Feb. 19, 2015

Related U.S. Application Data

(63) Continuation of application No. 14/108,236, filed on Dec. 16, 2013, which is a continuation of application No. 12/046,381, filed on Mar. 11, 2008, now Pat. No. 8,658,388, which is a continuation of application No. PCT/US2007/079002, filed on Sep. 20, 2007.

(60) Provisional application No. 60/913,087, filed on Apr. 20, 2007, provisional application No. 61/007,527, filed on Sep. 21, 2006.

(51) Int. Cl.
*C40B 30/08* (2006.01)
*G01N 33/574* (2006.01)
*G01N 33/542* (2006.01)
(Continued)

(52) U.S. Cl.
CPC .......... *G01N 33/574* (2013.01); *G01N 33/542* (2013.01); *G01N 33/57415* (2013.01); *G01N 33/582* (2013.01); *G01N 33/6845* (2013.01); *G01N 33/6854* (2013.01); *C40B 30/08* (2013.01); *G01N 2333/902* (2013.01); *G01N 2333/908* (2013.01)

(58) Field of Classification Search
None
See application file for complete search history.

(56) References Cited

U.S. PATENT DOCUMENTS

| 4,233,402 A | 11/1980 | Maggio et al. |
| 4,975,532 A | 12/1990 | Rowley et al. |

(Continued)

FOREIGN PATENT DOCUMENTS

| CA | 2 588 992 A1 | 6/2006 |
| EP | 0 310 132 A2 | 4/1989 |

(Continued)

OTHER PUBLICATIONS

Ahn, S. et al., "Molecular Markers for Individualized Therapy in Colorectal Cancer: Progress Towards a Pharmacogenomics Array," Curr Pharma and Personalized Medicine, 7:70-80, 2009.

(Continued)

*Primary Examiner* — Christian Boesen
(74) *Attorney, Agent, or Firm* — Kilpatrick Townsend & Stockton LLP

(57) ABSTRACT

The present invention provides antibody-based arrays for detecting the activation state and/or total amount of a plurality of signal transduction molecules in rare circulating cells and methods of use thereof for facilitating cancer prognosis and diagnosis and the design of personalized, targeted therapies.

20 Claims, 19 Drawing Sheets

(51) Int. Cl.
  *G01N 33/58* (2006.01)
  *G01N 33/68* (2006.01)

(56) References Cited

U.S. PATENT DOCUMENTS

| | | |
|---|---|---|
| 5,089,419 A | 2/1992 | Kuniyuki |
| 5,120,660 A | 6/1992 | Kuniyuki |
| 5,445,944 A | 8/1995 | Ullman |
| 5,516,931 A | 5/1996 | Giese et al. |
| 5,527,684 A | 6/1996 | Mabile et al. |
| 5,876,944 A | 3/1999 | Kuo |
| 6,201,109 B1 | 3/2001 | Avnur et al. |
| 6,335,173 B1 | 1/2002 | Kaplan |
| 6,406,913 B1 | 6/2002 | Ullman et al. |
| 6,511,809 B2 | 1/2003 | Baez et al. |
| 6,627,400 B1 | 9/2003 | Singh et al. |
| 6,649,351 B2 | 11/2003 | Matray et al. |
| 6,770,439 B2 | 8/2004 | Singh et al. |
| 6,818,399 B2 | 11/2004 | Singh et al. |
| 6,949,347 B2 | 9/2005 | Singh et al. |
| 6,972,198 B2 | 12/2005 | Craig et al. |
| 7,101,682 B2 | 9/2006 | Ullman et al. |
| 7,279,286 B2 | 10/2007 | Kannt et al. |
| 7,402,399 B2 | 7/2008 | Mukherjeei et al. |
| 7,537,938 B2 | 5/2009 | Kirakossian et al. |
| 7,695,924 B2 | 4/2010 | Perez et al. |
| 7,695,926 B2 | 4/2010 | Perez et al. |
| 8,163,499 B2 | 4/2012 | Singh et al. |
| 8,609,349 B2 | 12/2013 | Singh et al. |
| 2002/0142361 A1 | 10/2002 | Emmert-Buck |
| 2002/0168641 A1 | 11/2002 | Mortensen et al. |
| 2003/0059811 A1 | 3/2003 | Djaballah et al. |
| 2003/0087311 A1 | 5/2003 | Wolf |
| 2003/0153013 A1 | 8/2003 | Huang |
| 2003/0153014 A1 | 8/2003 | Shen et al. |
| 2003/0190689 A1 | 10/2003 | Crosby et al. |
| 2004/0077090 A1 | 4/2004 | Short |
| 2004/0106161 A1 | 6/2004 | Bossenmaier et al. |
| 2004/0157271 A1 | 8/2004 | Kirakossian et al. |
| 2004/0175696 A1 | 9/2004 | Ullman et al. |
| 2004/0235002 A1 | 11/2004 | Holmes et al. |
| 2004/0265923 A1 | 12/2004 | Gilmore et al. |
| 2004/0265938 A1 | 12/2004 | Remacle et al. |
| 2005/0069962 A1 | 3/2005 | Archer et al. |
| 2005/0153342 A1 | 7/2005 | Chen |
| 2006/0024723 A1 | 2/2006 | Hussa et al. |
| 2006/0024846 A1 | 2/2006 | Singh et al. |
| 2006/0127945 A1 | 6/2006 | Preaudat et al. |
| 2007/0111944 A1 | 5/2007 | Scrofani et al. |
| 2007/0269902 A1 | 11/2007 | Beechem et al. |
| 2008/0096235 A1 | 4/2008 | Kimberly et al. |
| 2008/0176229 A1 | 7/2008 | Agus et al. |
| 2008/0187948 A1 | 8/2008 | Chan-Hui et al. |
| 2008/0261829 A1 | 10/2008 | Harvey et al. |
| 2009/0035792 A1 | 2/2009 | Singh et al. |
| 2009/0124511 A1 | 5/2009 | Archer et al. |
| 2010/0021457 A1 | 1/2010 | Pfleger et al. |
| 2010/0167945 A1 | 7/2010 | Singh et al. |
| 2010/0311185 A1 | 12/2010 | Schelp et al. |
| 2011/0275097 A9 | 11/2011 | Singh et al. |
| 2011/0281748 A1 | 11/2011 | Singh et al. |
| 2012/0231965 A1 | 9/2012 | Kim et al. |
| 2012/0270745 A1 | 10/2012 | Singh et al. |
| 2013/0045880 A1 | 2/2013 | Singh et al. |
| 2013/0324430 A1 | 12/2013 | Kim et al. |
| 2014/0187445 A1 | 7/2014 | Harvey et al. |
| 2014/0349865 A1 | 11/2014 | Singh et al. |

FOREIGN PATENT DOCUMENTS

| | | | |
|---|---|---|---|
| EP | 1 145 004 B1 | 4/2004 | |
| EP | 1 673 635 B1 | 4/2009 | |
| EP | 2 065 475 A1 | 6/2009 | |
| JP | H06-109734 A | 4/1994 | |
| JP | 07-216000 A2 | 8/1995 | |
| JP | H10-501070 A | 1/1998 | |
| JP | 2002-214237 A | 7/2002 | |
| JP | 2002-530629 | 9/2002 | |
| JP | 2005-500045 | 1/2005 | |
| JP | 2007-510910 | 4/2007 | |
| JP | 2008-292424 A | 12/2008 | |
| RU | 2149404 C1 | 5/2000 | |
| RU | 2165081 C | 4/2001 | |
| WO | 96/07103 A1 | 3/1996 | |
| WO | 00/29609 | 5/2000 | |
| WO | 01/27611 A2 | 4/2001 | |
| WO | 02/090964 A1 | 11/2002 | |
| WO | 03/006104 | 1/2003 | |
| WO | 03/087761 A2 | 10/2003 | |
| WO | 2004/071572 A2 | 8/2004 | |
| WO | 2005/044794 | 5/2005 | |
| WO | 2005/095965 A1 | 10/2005 | |
| WO | 2006/031815 A2 * | 3/2006 | ............... C12Q 1/68 |
| WO | 2006/044748 A2 | 4/2006 | |
| WO | 2006/045991 A1 | 5/2006 | |
| WO | 2006/054991 A | 5/2006 | |
| WO | 2006/055739 A2 | 5/2006 | |
| WO | 2006/105642 A1 | 10/2006 | |
| WO | 2006/119980 A1 | 11/2006 | |
| WO | 2007/130677 A2 | 11/2007 | |
| WO | 2008/019375 A2 | 2/2008 | |
| WO | 2008/036802 A2 | 3/2008 | |
| WO | 2008/064884 A1 | 6/2008 | |
| WO | 2009/012140 A2 | 1/2009 | |
| WO | 2009/108637 A1 | 9/2009 | |
| WO | 2011/008990 A1 | 1/2011 | |

OTHER PUBLICATIONS

Angenendt, P. et al. "3D Protein microarrays: performing multiplex immunoassays on a single Chip," Anal. Chem., 75:4368-4372, 2003.
Annex to EPO Form 2004, Communication Pursuant to Rule 71(3) EPC; European Patent Application No. 07 842 865.3; May 8, 2012 (7 pgs).
Arpino, G. et al., "Infiltrating lobular carcinoma of the breast: tumor characteristics and clinical outcome," Breast Cancer Research, 6:R149-156, 2003.
Bachleitner-Hofmann, T. et al., "HER kinase activation confers resistance to MET tyrosine kinase inhibition in MET oncogene-addicted gastric cancer cells," Molecular Cancer Therapeutics, 7(11):3499-3508, 2008.
Bartling, B. et al., "Comparative application of antibody and gene array for expression profiling in human squamous cell lung carcinoma," Lung Cancer, 49(2):145-154, 2005.
Becker et al., "Role of receptor tyrosine kinases in gastric cancer: new targets for a selective therapy," World J of Gastroenterol, 12(21):3297-3305, 2006.
Blume-Jensen, P. and Hunter, T., "Oncogenic kinase signalling," Nature, 411:355-365, 2001.
Daly et al., "Evaluating concentration estimation errors in ELISA microarray experiments," BMC Bioinformatics, 6:17, 2005, printed as pp. 1/11 to 11/11.
Dorland's Medical Dictionary for Healthcare Consumers (non-small cell carcinoma, Merck Sharp & Dohme Corp.) 2007, 1 page.
Engelman, J. et al., "ErbB-3 mediates phosphoinositide 3-kinase activity in gefitinib-sensitive non-small cell lung cancer cell lines," PNAS, 102(10):3788-93, 2005.
Engelman, J. et al., "Met amplification leads to gefitinib resistance in lung cancer by activating ERBB3 signaling," Science, 316(5827):1039-1043, 2007.
Fiore et al., "Clinical relevance of KRAS mutation detection in metastatic colorectal cancer treated by Cetuximab plus chemotherapy," British Journal of Cancer 96:1166-69, 2007.
Gembitsky, D. et al., "A prototype antibody microarray platform to monitor changes in protein tyrosine phosphorylation," Molecular & Cellular Proteomics, 3(11):1102-1118, 2004.
Glucose Oxidase (MeSH http://www.ncbi.nlm.nih.gov/mesh/?term=glucose+oxidase, 1964), "MeSH".
Haab, B., "Antibody arrays in cancer research, " Molecular & Cellular Proteomics, 4(4):377-383, 2005.

(56) References Cited

OTHER PUBLICATIONS

Haab, B., "Applications of antibody array platforms," Current Opinion in Biotechnology, 17:415-421, 2006.
Huang, F. et al., "The mechanisms of differential sensitivity to an insulin-like growth factor-1 receptor inhibitor (BMS-536924) and rationale for combining with EGFR/HER2 inhibitors," Cancer Research, 69(1):161-170, 2009.
Hudelist, G. et al. "Use of high-throughput protein array for profiling of differentially expressed proteins in normal and malignant breast tissue," Breast Cancer Research and Treatment, 86:281-291, 2004.
Humblet, Y., "Cetuximab: an $IgG_1$ monoclonal antibody for the treatment of epidermal growth factor receptor-expressing tumours," Expert Opin. Pharmacother, 5(7): 1621-1633, 2004.
Kelkar, S. et al., "Cytoplasmic Dynein Mediates Adenovirus Binding to Microtubules," J. Virol., 78(18):10122-10132, 2004.
Kim, P. et al., "Highly sensitive proximity mediated immunoassay reveals HER2 status conversion in the circulating tumor cells of metastatic breast cancer patients," Proteome Science, 9:75, 2011, 15 pgs.
Kopf, E. et al. "Antibody arrays—An emerging tool in cancer proteomics," The International Journal of Biochemistry & Cell Biology, 39:1305-1317, 2007.
Kuhlmann, W.D. et al., "Glucose oxidase as label in histological immunoassays with enzyme-amplification in a two-step technique: coimmobilized horseradish peroxidase as secondary system enzyme for chromogen oxidation," Histochemistry, 85:13-17, 1986.
Langer, C.J., "Emerging Role of Epidermal Growth Factor Receptor Inhibition in Therapy for Advanced Malignancy: Focus on Nsclc," Int. J. Radiation Oncology boil. Phys., 58(3):991-1002, 2004.
Langry, K. et al., "Chemiluminescence assay for the detection of biological warfare agents," U.S. Dept. of Energy Report No. UCRL-ID-136797, Nov. 5, 1999, 30 pages.
Litt et al., Chapter 10, "Tyramide signal amplification: applications in detecting infectious agents," in Rapid Detection of Infectious Agents, Ed. Specter et al., Plenum Press, New York, 1998, pp. 159-173.
Lu, Z. et al., "Construction of an antibody microarray based on agarose-coated slides," Electrophoresis, 28:406-413, 2007.
Mouridsen, H. et al., "Phase III study of letrozole versus tamoxifen as first line therapy of advanced breast cancer in postmenopausal women: analysis of survival and update of efficiency from the international letrozole breast cancer group," Journal of Clinical Oncology, 21:2101-2109, 2003.
Nielsen, U. et al. "Profiling receptor tyrosine kinase activation by using Ab microarrays," PNAS, 100(16):9330-9335, 2003.
Nielsen, U. et al. "Multiplexed sandwich assays in microarray format," Journal of Immunological Methods, 290:107-120, 2004.
Pearce, S. et al., "Modulation of estrogen receptor a function and stability by tamoxifen and a critical amino acid (asp-538) in helix 12," Journal of Biological Chemistry, 278:7630-7638, 2003.
Restriction Requirement mailed on Jun. 25, 2010 in U.S. Appl. No. 12/046,381; Filing Date: Mar. 11, 2008; 12 pages.
Samuilov, V.D., Immunofermentnyi analiz [Immunoenzyme analysis], Sorosovskii obrazovatelnyi zhurnal, 12:9-15, 1999.
Sanchez-Carbayo, M., "Antibody arrays: technical considerations and clinical applications in cancer," Clinical Chemistry, 52:1651-1659, 2006.
Sathyanarayanan, S. et al., "229 Anti-IGF1R therapy with dalotuzumab is efficacious in a sub-set of KRAS mutant cetuximab refractory CRC models," Eur J Cancer, Supplement, 8(7):75, Nov. 16, 2010, p. 75.
Scaltriti, M. et al., "Expression of p95HER2, a truncated form of the HER2 receptor and response to anti-HER2 therapies in breast cancer," Journal of the National Cancer Institute, 99(8):628-638, 2007.
Siena, Salvatore et al., "Biomarkers Predicting Clinical Outcome of Epidermal Growth Factor Receptor-Targeted Therapy in Metastatic Colorectal Cancer," J Natl Cancer Inst, 101(19):1308-1324, 2009.
Stern, David F., "Phosphoproteomics for Oncology discovery and treatment," Expert Opinion on Therapeutic Targets, 9(4):851-860, 2005.
Ubersax et al., "Mechanisms of specificity in protein phosphorylation," Nature, 8:530-541, 2007.
Wiese et al., "Simultaneous multianylyte ELISA performed on a microarray platform," Clinical Chemistry, 47(8):1450-1457, 2001.
Woodbury et al., "Elevated HGF levels in sera from breast cancer patients detected using a protein microarray ELISA," Journal of Proteome Research, 1:233-237, 2002.
Yan, Jing et al., "Role of antibody chip in analysis of inflammatory cytokine expression in severe sepsis," Chin. J. Emerg. Med., 15(9):830-833, 2006.
Yonemura, Y. et al., "Role of vascular endothelial growth factor C expression in the development of lymph node metastasis in gastric cancer," Clinical Cancer Research, 5:1823-1829, 1999.
Zhou, B. et al., "Targeting Adam-mediated ligand cleavage to inhibit HER3 and EGFR pathways in non-small cell lung cancer," Cancer Cell, 10:39-50, 2006.
Yasui, W. et al., "Expression of epidermal growth factor receptor in human gastric and colonic carcinomas," Cancer Res, Jan. 1, 1988, 48(1), 137-141.

* cited by examiner

FIG. 3A
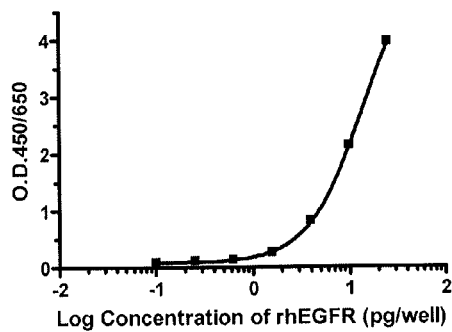
FIG. 3B
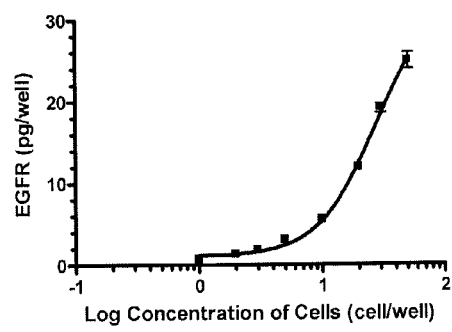
FIG. 3C
| Cells/well | EGFR (pg/well) | EGFR (pg/cell) |
|---|---|---|
| 50 | 25.00±1.40 | 0.50 |
| 30 | 19.20±0.83 | 0.64 |
| 20 | 11.87±0.08 | 0.59 |
| 10 | 5.49±0.251 | 0.55 |
| 5 | 3.00±0.016 | 0.60 |
| 3 | 1.75±0.019 | 0.58 |
| 2 | 1.28±0.068 | 0.64 |
| 1 | 0.66±0.012 | 0.66 |

- Capture Ab, 0.25ug/ml
- 0.125ug/ml
- 0.0625ug/ml

| S/N ratio cell/well | Capture Ab Concentration | | |
|---|---|---|---|
| | 0.25ug/ml | 0.125ug/ml | 0.0625ug/ml |
| 1,000 | 9.10 | 19.71 | 36.12 |
| 333 | 8.57 | 19.17 | 34.02 |
| 111 | 7.58 | 15.70 | 27.27 |
| 37 | 5.38 | 9.81 | 16.15 |
| 12 | 3.47 | 4.88 | 5.98 |
| 4 | 2.16 | 2.33 | 2.60 |
| 1 | 1.60 | 1.53 | 1.78 |
| 0 | 1.00 | 1.00 | 1.00 |

| Cell/well | O.D.450/650 | | Mean | S/N ratio |
|---|---|---|---|---|
| 1,000.00 | 2.47 | 2.208 | 2.339 | 668.29 |
| 333.33 | 2.432 | 2.363 | 2.3975 | 685.00 |
| 111.11 | 2.019 | 2.048 | 2.0335 | 581.00 |
| 37.04 | 1.255 | 1.386 | 1.3205 | 377.29 |
| 12.35 | 0.393 | 0.435 | 0.414 | 118.29 |
| 4.12 | 0.04 | 0.037 | 0.0385 | 11.00 |
| 1.37 | 0.012 | 0.007 | 0.0095 | 2.71 |
| 0 | 0.004 | 0.003 | 0.0035 | 1.00 |

| Cells/well | O.D.450/650 | | S/N ratio |
|---|---|---|---|
| 500 | 2.135 | 2.143 | 30.56 |
| 200 | 2.002 | 2.035 | 28.84 |
| 100 | 1.796 | 1.818 | 25.81 |
| 50 | 1.489 | 1.483 | 21.23 |
| 20 | 0.956 | 0.915 | 13.36 |
| 10 | 0.495 | 0.487 | 7.01 |
| 5 | 0.208 | 0.216 | 3.03 |
| 0 | 0.07 | 0.07 | 1.00 |

FIG. 7A
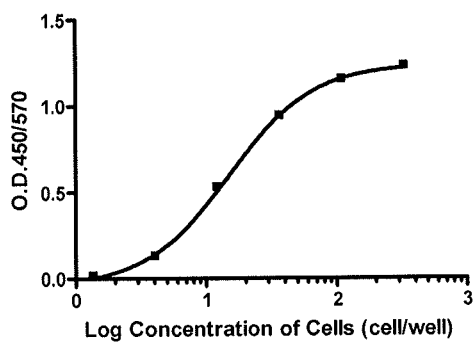
FIG. 7B
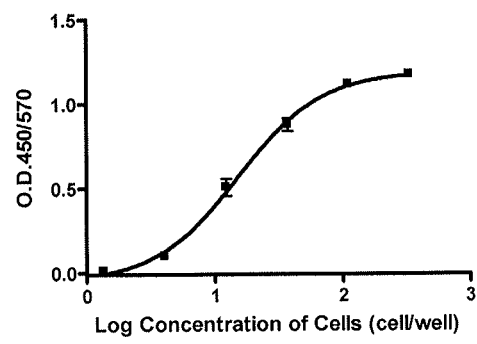
FIG. 7C
| Cells (cell/well) | Total Erk2 (O.D.450/570) | | S/N ratio | Phospho-Erk2 (O.D.450/570) | | S/N ratio |
|---|---|---|---|---|---|---|
| 1000 | 1.097 | 1.076 | 271.63 | 1.086 | 1.054 | 356.67 |
| 333.3333 | 1.241 | 1.214 | 306.88 | 1.193 | 1.144 | 389.50 |
| 111.1111 | 1.163 | 1.141 | 288.00 | 1.136 | 1.087 | 370.50 |
| 37.03704 | 0.958 | 0.923 | 235.13 | 0.913 | 0.838 | 291.83 |
| 12.34568 | 0.52 | 0.533 | 131.63 | 0.555 | 0.455 | 168.33 |
| 4.115226 | 0.114 | 0.139 | 31.63 | 0.102 | 0.093 | 32.50 |
| 1.371742 | 0.016 | 0.01 | 3.25 | 0.012 | 0.007 | 3.17 |
| 0 | 0.004 | 0.004 | 1.00 | 0.003 | 0.003 | 1.00 |

FIG. 8A
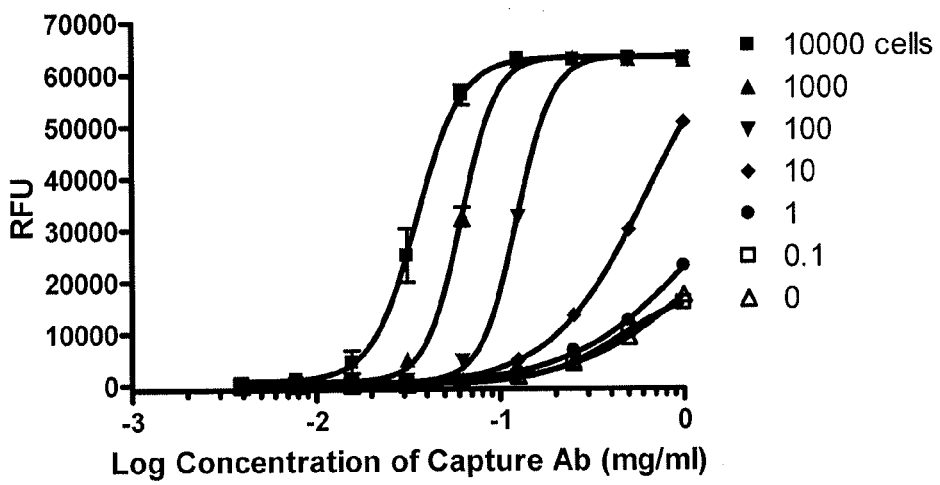
FIG. 8B
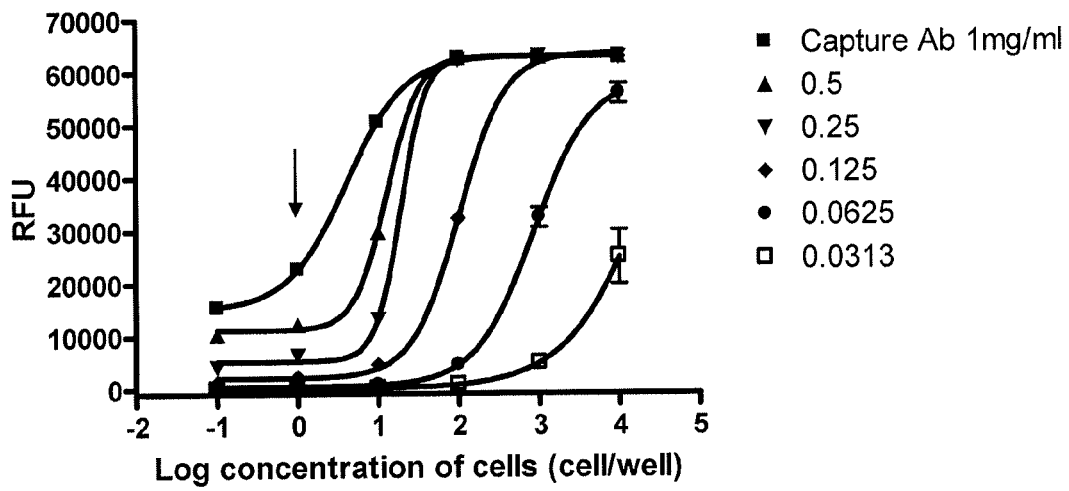
FIG. 8C
| S/N ratio Cell/well | Capture Ab Concentration | | | | |
|---|---|---|---|---|---|
| | 1mg/ml | 0.5mg/ml | 0.25mg/ml | 0.125mg/ml | 0.0625mg/ml |
| 0.1 cell | 0.90 | 1.15 | 1.03 | 0.86 | 1.17 |
| 1 cell | 1.32 | 1.35 | 1.59 | 1.50 | 2.11 |
| 10 cell | 2.94 | 3.30 | 3.30 | 3.07 | 3.14 |
| 100 cell | 3.64 | 6.95 | 15.52 | 21.35 | 16.52 |
| 1000 cell | 3.63 | 6.96 | 15.69 | 41.34 | 118.78 |
| 10000 cell | 3.66 | 6.98 | 15.63 | 41.57 | 204.97 |

FIG. 9A
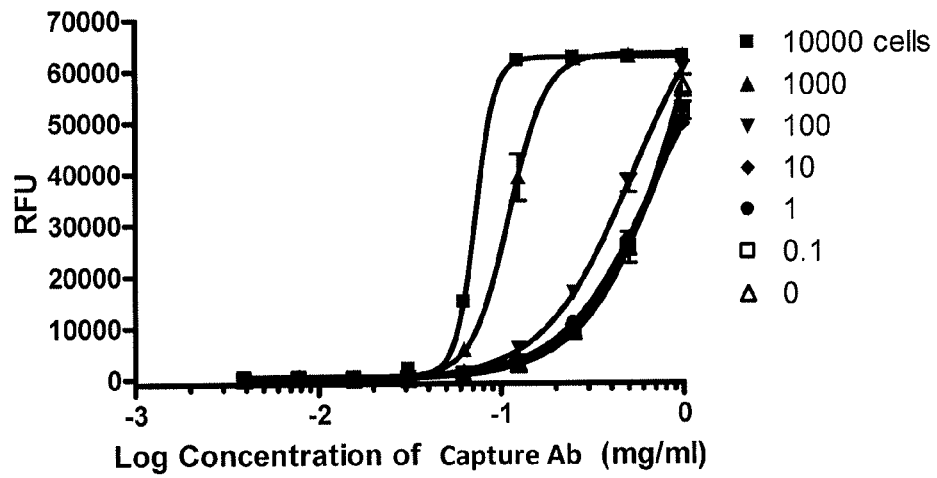
FIG. 9B
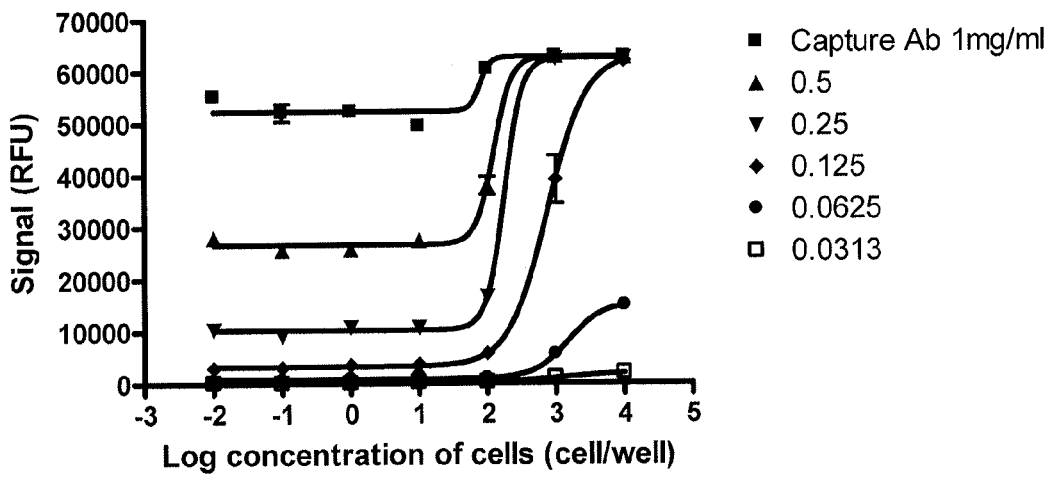
FIG. 9C
| S/N ratio Cell/well | Capture Ab Concentration | | | | |
|---|---|---|---|---|---|
| | 1mg/ml | 0.5mg/ml | 0.25mg/ml | 0.125mg/ml | 0.0625mg/ml |
| 0.1 cell | 0.91 | 1.01 | 1.01 | 1.15 | 1.16 |
| 1 cell | 0.92 | 1.01 | 1.20 | → 1.33 | 1.59 |
| 10 cell | 0.87 | 1.08 | 1.20 | 1.39 | 2.46 |
| 100 cell | 1.06 | 1.49 | 1.85 | 2.16 | 1.70 |
| 1000 cel | 1.10 | 2.47 | 6.92 | 14.63 | 9.29 |
| 10000 cell | 1.10 | 2.46 | 6.94 | 23.17 | 24.79 |

FIG. 10A
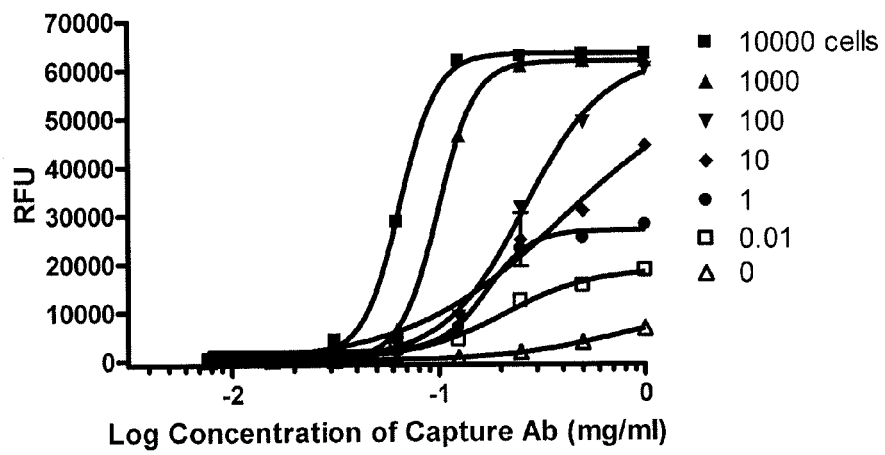
FIG. 10B
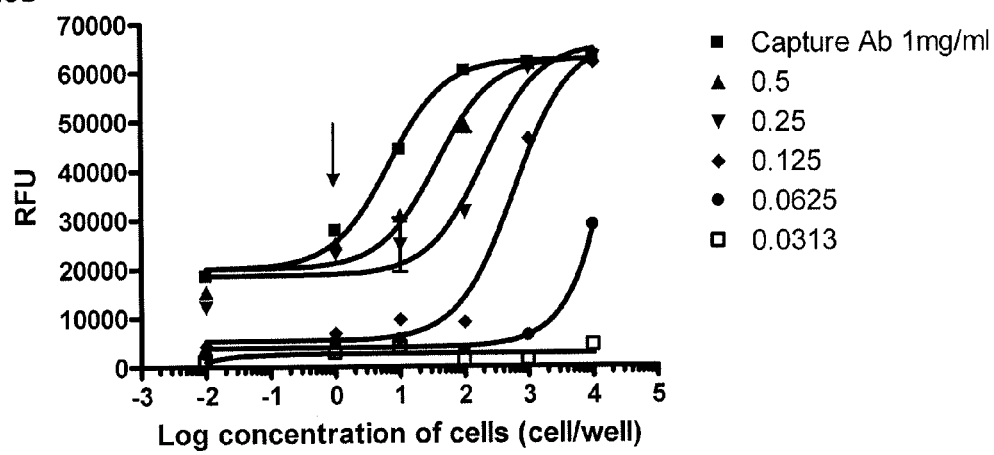
FIG. 10C
| S/N ratio Cell/well | Capture Ab Concentration | | | | |
|---|---|---|---|---|---|
| | 1mg/ml | 0.5mg/ml | 0.25mg/ml | 0.125mg/ml | 0.0625mg/ml |
| 0.01 cell | 2.86 | 4.26 | 7.59 | 9.40 | 16.23 |
| 1 cell | 4.31 | 7.00 | 14.34 | 15.27 | 32.21 |
| 10 cell | 6.84 | 8.56 | 15.49 | 21.74 | 35.90 |
| 100 cell | 9.32 | 13.66 | 19.58 | 20.24 | 21.30 |
| 1000 cell | 9.58 | 17.19 | 37.90 | 104.95 | 40.58 |
| 10000 cell | 9.79 | 17.55 | 39.15 | 139.96 | 188.23 |

FIG. 11A
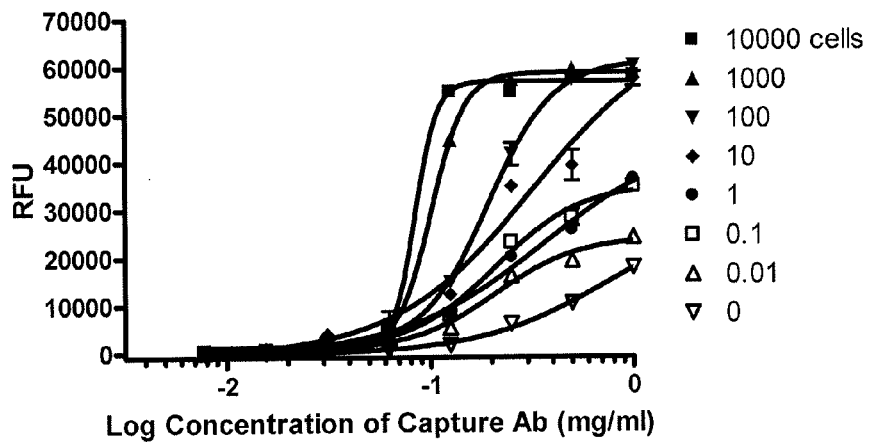
FIG. 11B
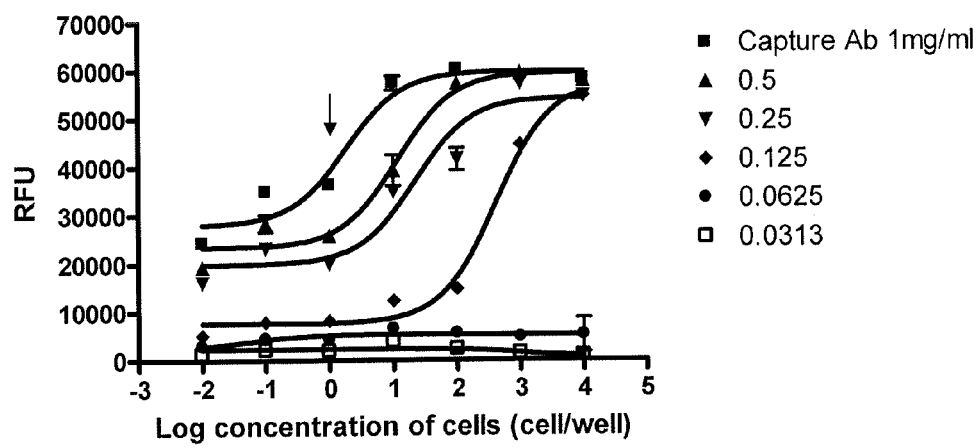
FIG. 11C
| S/N ratio Cell/well | Capture Ab Concentration | | | | |
|---|---|---|---|---|---|
| | 1mg/ml | 0.5mg/ml | 0.25mg/ml | 0.125mg/ml | 0.0625mg/ml |
| 0.01 cell | 1.36 | 1.87 | 2.69 | 3.47 | 5.22 |
| 0.1 cell | 1.95 | 2.74 | 3.86 | 5.24 | 8.01 |
| 1 cell | 2.04 | 2.49 | 3.34 | → 5.45 | 7.62 |
| 10 cell | 3.21 | 3.79 | 5.81 | 8.21 | 11.72 |
| 100 cell | 3.37 | 5.54 | 6.93 | 9.86 | 9.99 |
| 1000 cell | 3.29 | 5.75 | 9.54 | 29.81 | 8.53 |
| 10000 cell | 3.26 | 5.59 | 9.11 | 36.63 | 9.34 |

Alexa 647　　　　　　　Alexa 555

─◆─ t-EGFR direct ─■─ p-EGFR direct ─▲─ p-EGFR proximity

ANTIBODY-BASED ARRAYS FOR DETECTING MULTIPLE SIGNAL TRANSDUCERS IN RARE CIRCULATING CELLS

CROSS-REFERENCE TO RELATED APPLICATIONS

The present application is a continuation of U.S. application Ser. No. 14/108,236, filed Dec. 16, 2013, which application is a continuation of U.S. application Ser. No. 12/046,381, filed Mar. 11, 2008, which issued on Feb. 25, 2014 under U.S. Pat. No. 8,658,388 B2, which application is a continuation application of PCT/US07/79002, filed Sep. 20, 2007, which application claims the benefit of priority of U.S. Provisional Application No. 61/007,527, filed Sep. 21, 2006 and U.S. Provisional Application No. 60/913,087, filed Apr. 20, 2007, the disclosures of which are hereby incorporated by reference in their entirety for all purposes.

BACKGROUND OF THE INVENTION

Tumor cells are often found in the blood of patients with various early stages of cancer as "micrometastases" (disseminated tumor cells), and are also found in metastatic cancers. The number of tumor cells in blood depends on the stage and type of the tumor. Tumors are extremely heterogeneous. As a result, a biopsy from a single site might not represent the heterogeneity in a tumor population. Biopsies are typically obtained on primary tumors; however, most metastatic tumors are not biopsied, making molecular analysis of tumor samples even more difficult.

During tumor metastasis, the most aggressive tumor cells leave the primary tumor and travel through the blood and lymphatic system to reach a distant location. Thus, circulating tumor cells from blood represent the most aggressive and homogenous population of tumor cells. The number of metastatic tumor cells in blood can vary from one to several thousand cells per milliliter of blood. Accordingly, specific and sensitive methods are needed to detect these cells for diagnostic and prognostic purposes. The present invention satisfies this need and provides related advantages as well.

BRIEF SUMMARY OF THE INVENTION

The present invention provides antibody-based arrays for detecting the activation state and/or total amount of a plurality of signal transduction molecules in rare circulating cells and methods of use thereof, which have the advantages of specificity associated with enzyme-linked immunosorbent assays, sensitivity associated with signal amplification, and high-throughput multiplexing associated with microarrays.

In one aspect, the present invention provides an array having superior dynamic range comprising a plurality of dilution series of capture antibodies specific for one or more analytes in a cellular extract, wherein the capture antibodies are restrained on a solid support.

In another aspect, the present invention provides a method for performing a multiplex, high-throughput immunoassay having superior dynamic range, the method comprising:
(a) incubating a cellular extract with a plurality of dilution series of capture antibodies specific for one or more analytes in the cellular extract to form a plurality of captured analytes, wherein the capture antibodies are restrained on a solid support;
(b) incubating the plurality of captured analytes with detection antibodies specific for the corresponding analytes to form a plurality of detectable captured analytes;
(c) incubating the plurality of detectable captured analytes with first and second members of a signal amplification pair to generate an amplified signal; and
(d) detecting an amplified signal generated from the first and second members of the signal amplification pair.

In yet another aspect, the present invention provides a method for performing a multiplex, high-throughput immunoassay having superior dynamic range, the method comprising:
(a) incubating a cellular extract with a plurality of dilution series of capture antibodies specific for one or more analytes in the cellular extract to form a plurality of captured analytes, wherein the capture antibodies are restrained on a solid support;
(b) incubating the plurality of captured analytes with detection antibodies specific for the corresponding analytes to form a plurality of detectable captured analytes, wherein the detection antibodies comprise:
  (1) a plurality of activation state-independent antibodies labeled with a facilitating moiety, and
  (2) a plurality of activation state-dependent antibodies labeled with a first member of a signal amplification pair,
  wherein the facilitating moiety generates an oxidizing agent which channels to and reacts with the first member of the signal amplification pair;
(c) incubating the plurality of detectable captured analytes with a second member of the signal amplification pair to generate an amplified signal; and
(d) detecting the amplified signal generated from the first and second members of the signal amplification pair.

The present invention also provides kits for performing the antibody-based array methods described above comprising: (a) a dilution series of a plurality of capture antibodies restrained on a solid support; and (b) a plurality of detection antibodies. The kits can optionally further comprise other reagents such as, for example, the first and second members of the signal amplification pair.

Other objects, features, and advantages of the present invention will be apparent to one of skill in the art from the following detailed description and figures.

BRIEF DESCRIPTION OF THE DRAWINGS

FIGS. 3A-C show the detection of total EGFR in A431 cells using monoclonal antibodies against the extracellular domain of EGFR as the capture antibody and detection antibody in an ELISA. FIG. 3A: Standard curve of the sandwich ELISA. The sensitivity was about 0.25 pg/well using a recombinant extracellular domain of human EGFR. FIG. 3B: Cell titration curve. The EGFR concentration in A431 cells was detected by ELISA. FIG. 3C: Table of EGFR concentration calculated in pg/well and pg/cell. The calculated EGFR concentration was about 0.6 pg in each A431 cell.

FIG. 4A: Cell titration curve with a dilution series of the capture antibody. FIG. 4B: Table of signal/noise (S/N) ratio between cells and background. The signal/noise ratio was 1.78 at the one cell level when the capture antibody concentration was 0.0625 µg/ml.

FIG. 5A: Cell titration of total ErBb2 in SKBr3 cells. The detection range was between about 1,000 cells and about 1.37 cells. FIG. 5B: Table of signal/noise (S/N) ratio between cells and background. The signal/noise ratio was 2.71 at the 1.37 cell level when the capture antibody concentration was 1 µg/ml.

FIG. 6A: Cell titration of phosphorylated ErBb2 in SKBr3 cells. The detection range was between about 500 cells and about 5 cells. FIG. 6B: Table of signal/noise (S/N) ratio between cells and background. The signal/noise ratio was 3.03 at the 5 cell level when the capture antibody concentration was 1 µg/ml.

FIGS. 7A-C show the detection of total and phosphorylated Erk2 protein in SKBr3 cells using monoclonal antibodies against Erk2 as the capture antibody and detection antibody in an ELISA. FIG. 7A: Detection of total Erk2 protein using monoclonal antibodies against Erk2 as the capture antibody and detection antibody. FIG. 7B: Detection of phosphorylated Erk2 protein using a monoclonal antibody against Erk2 as the capture antibody and a monoclonal antibody against phosphorylated Erk2 as the detection antibody. FIG. 7C: Table of signal/noise (S/N) ratio between cells and background. The signal/noise ratio was about 3 at the 1.37 cell level for both total and phosphorylated Erk2.

FIGS. 8A-C show the detection of total EGFR in A431 cells using monoclonal antibodies against the extracellular domain of EGFR as the capture antibody and detection antibody in a microarray ELISA. FIG. 8A: Capture antibody dilution curve based on cell numbers. The microarray ELISA had a wide dynamic range to detect EGFR in about 1-10,000 cells with various concentrations of capture antibody in the dilution series. FIG. 8B: Cell titration curve based upon the dilution series of capture antibody concentrations, which showed that EGFR could be detected from one cell (arrow). FIG. 8C: Table of signal/noise (S/N) ratio between cells and background at various capture antibody concentrations in the dilution series. The signal/noise ratio was 2.11 at the one cell level when the capture antibody concentration was 0.0625 mg/ml (arrow).

FIGS. 9A-C show the detection of phosphorylated EGFR in A431 cells using a monoclonal antibody against the extracellular domain of EGFR as the capture antibody and a monoclonal antibody against phosphorylated EGFR as the detection antibody in a microarray ELISA. FIG. 9A: Capture antibody dilution curve based on cell numbers. The microarray ELISA had a wide dynamic range to detect phosphorylated EGFR in about 1-10,000 cells with various concentrations of capture antibody in the dilution series. FIG. 9B: Cell titration curve based upon the dilution series of capture antibody concentrations, which showed that phosphorylated EGFR could be detected from one cell. FIG. 9C: Table of signal/noise (S/N) ratio between cells and background at various capture antibody concentrations in the dilution series. The signal/noise ratio was 1.33 at the one cell level when the capture antibody concentration was 0.125 mg/ml (arrow).

FIGS. 10A-C show the detection of total ErBb2 in SKBr3 cells using monoclonal antibodies against the extracellular domain of ErBb2 as the capture antibody and detection antibody in a microarray ELISA. FIG. 10A: Capture antibody dilution curve based on cell numbers. The microarray ELISA had a wide dynamic range to detect ErBb2 in about 1-10,000 cells with various concentrations of capture antibody in the dilution series. FIG. 10B: Cell titration curve based upon the dilution series of capture antibody concentrations, which showed that ErBb2 could be detected from one cell (arrow). FIG. 10C: Table of signal/noise (S/N) ratio between cells and background at various capture antibody concentrations in the dilution series. The signal/noise ratio was 15.27 at the one cell level when the capture antibody concentration was 0.125 mg/ml (arrow).

FIGS. 11A-C shows the detection of phosphorylated ErBb2 in SKBr3 cells using a monoclonal antibody against the extracellular domain of ErBb2 as the capture antibody and a monoclonal antibody against phosphorylated ErBb2 as the detection antibody in a microarray ELISA. FIG. 11A: Capture antibody dilution curve based on cell numbers. The microarray ELISA had a wide dynamic range to detect ErBb2 in about 1-10,000 cells with various concentrations of capture antibody in the dilution series. FIG. 11B: Cell titration curve based upon the dilution series of capture antibody concentrations, which showed that phosphorylated ErBb2 could be detected from one cell (arrow). FIG. 11C: Table of signal/noise (S/N) ratio between cells and background at various capture antibody concentrations in the dilution series. The signal/noise ratio was 5.45 at the one cell level when the capture antibody concentration was 0.125 mg/ml (arrow).

FIG. 13A: Titration curves of phosphorylated EGFR in A431 cells at various capture antibody concentrations in the single detector format. Very high background was observed due to the lack of specificity of the single detection antibody in this format. FIG. 13B: Titration curves of phosphorylated EGFR in A431 cells at various capture antibody concentrations in the proximity dual detector format. Very low background was observed due to the increased specificity obtained by detecting the proximity between two detection antibodies in this format.

FIG. 17A: The microarray spotting pattern of various GO-oligonucleotide fractions is shown. FIG. 17B: The Alexa 647-oligonucleotide-conjugated antibodies had the highest binding affinity for the GO-oligonucleotides in fractions 13-15.

FIG. 19A: Total EGFR present in 10,000 cells was detected by the Alexa 647 signal generated from the Alexa 647-oligonucleotide-conjugated anti-EGFR antibody. The degree of EGFR phosphorylation was detected by monitoring the tyramide-mediated amplified Alexa 555 signal. FIG. 19B: Total EGFR (t-EGFR) was detected by a direct binding assay from as few as 10 cells and phosphorylated EGFR (p-EGFR) was detected from 1 cell. $10e^5$ p-EGFR molecules were detected with the proximity signal amplification method. The detection limit of p-EGFR was increased over 100-fold by using the proximity assay format.

DETAILED DESCRIPTION OF THE INVENTION

I. Introduction

Figure 1:
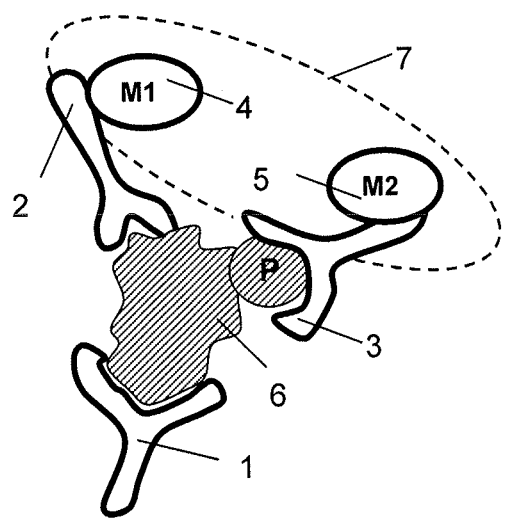
FIG. 1 shows three antibodies specifically bound to an activated analyte.

The present invention provides methods for detecting the activation state and/or total amount of a plurality of signal transduction molecules in rare circulating cells using an antibody-based array assay system. In some embodiments, the multiplex, high-throughput immunoassays of the present invention can detect the activation state of one or more signal transduction molecules in circulating cells of a solid tumor at the single cell level. In fact, signal transduction molecules such as EGFR can be detected with a sensitivity of about 100 zeptomoles and a linear dynamic range of from about 100 zeptomoles to about 100 femtomoles. As such, single-cell detection of the activation state of multiple signal transducers in rare circulating cells facilitates cancer prognosis and diagnosis as well as the design of personalized, targeted therapies.

Rare circulating cells include circulating cells of a solid tumor that have either metastasized or micrometastasized from a solid tumor. Circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells are some examples of circulating cells of a solid tumor.

Signal transduction molecules of interest are typically extracted shortly after the circulating cells are isolated to preserve their in situ activation state, preferably within about 24, 6, or 1 hr, and more preferably within about 30, 15 or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., Cell, 118:217-228 (2004)).

As explained in greater detail herein, to evaluate potential anticancer therapies for an individual patient, the isolated cells can be incubated with one or more anticancer drugs at varying doses. Growth factor stimulation can then be performed for a few minutes (e.g., about 1-5 minutes) or for several hours (e.g., about 1-6 hours). The differential activation of signaling pathways with and without anticancer drugs can aid in the selection of a suitable cancer therapy at the proper dose for each individual patent. Circulating cells can also be isolated from a patient sample during anticancer drug treatment and stimulated with one or more growth factors to determine whether a change in therapy should be implemented. As such, the methods of the present invention advantageously assist the clinician in providing the right anticancer drug at the right dose at the right time for every patient.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells.

The term "analyte" includes any molecule of interest, typically a macromolecule such as a polypeptide, whose presence, amount, and/or identity is determined. In certain instances, the analyte is a cellular component of circulating cells of a solid tumor, preferably a signal transduction molecule.

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay of the present invention to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR-1/FLT-1, VEGFR-2/FLK-1/KDR, VEGFR-3/FLT-4, FLT-3/FLK-2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, MET, RON, EPHA 1-8, EPHB 1-6, AXL, MER, TYRO3, TIE 1-2, TEK, RYK, DDR 1-2, RET, c-ROS, LTK (leukocyte tyrosine kinase), ALK (anaplastic lymphoma kinase), ROR 1-2, MUSK, AATYK 1-3, and RTK 106; non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as Akt, MAPK/ERK, MEK, RAF, PLA2, MEKK, JNKK, JNK, p38, Shc (p66), PI3K, Ras (e.g., K-Ras, N-Ras, H-Ras), Rho, Rac1, Cdc42, PLC, PKC, p70 S6 kinase, p53, cyclin D1, STAT1, STAT3, PIP2, PIP3, PDK, mTOR, BAD, p21, p27, ROCK, IP3, TSP-1, NOS, PTEN, RSK 1-3, JNK, c-Jun, Rb, CREB, Ki67, and paxillin; and combinations thereof.

As used herein, the term "circulating cells" comprises cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.).

The term "sample" as used herein includes any biological specimen obtained from a patient. Samples include, without limitation, whole blood, plasma, serum, red blood cells, white blood cells (e.g., peripheral blood mononuclear cells), saliva, urine, stool (i.e., feces), sputum, bronchial lavage fluid, tears, nipple aspirate, lymph (e.g., disseminated tumor cells of the lymph node), fine needle aspirate, any other bodily fluid, a tissue sample (e.g., tumor tissue) such as a biopsy of a tumor (e.g., needle biopsy), and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art and preparing a cellular extract of the circulating cells. In other embodiments, the sample is a formalin fixed paraffin embedded (FFPE) tumor tissue sample, e.g., from a solid tumor of the lung, colon, or rectum.

The term "subject" or "patient" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays of the present invention typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract of circulating cells of a solid tumor. In preferred embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, Akt, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. Non-limiting examples of activation states (listed in parentheses) that are suitable for detection with activation state-dependent antibodies include: EGFR (EGFRvIII, phosphorylated (p-) EGFR, EGFR:Shc, ubiquitinated (u-) EGFR, p-EGFRvIII); ErbB2 (p85:truncated (Tr)-ErbB2, p-ErbB2, p85:Tr-p-ErbB2, Her2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); IGF-1R (p-IGF-1R, IGF-1R:IRS, IRS:PI3K, p-IRS, IGF-1R:PI3K); INSR (p-INSR); KIT (p-KIT); FLT3 (p-FLT3); HGFR1 (p-HGFR1); HGFR2 (p-HGFR2); RET (p-RET); PDGFRa (p-PDGFRa); PDGFRP (p-PDGFRP); VEGFR1 (p-VEGFR1, VEGFR1:PLCγ, VEGFR1:Src); VEGFR2 (p-VEGFR2, VEGFR2:PLCγ, VEGFR2:Src, VEGFR2:heparin sulfate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); Tie1 (p-Tie1); Tie2 (p-Tie2); EphA (p-EphA); EphB (p-EphB);

NFKB and/or IKB (p-IK (S32), p-NFKB (S536), p-P65: IKBa); Akt (p-Akt (T308, S473)); PTEN (p-PTEN); Bad (p-Bad (S112, S136), Bad:14-3-3); mTor (p-mTor (S2448)); p70S6K (p-p70S6K (T229, T389)); Mek (p-Mek (S217, S221)); Erk (p-Erk (T202, Y204)); Rsk-1 (p-Rsk-1 (T357, S363)); Jnk (p-Jnk (T183, Y185)); P38 (p-P38 (T180, Y182)); Stat3 (p-Stat-3 (Y705, S727)); Fak (p-Fak (Y576)); Rb (p-Rb (S249, T252, S780)); Ki67; p53 (p-p53 (S392, S20)); CREB (p-CREB (S133)); c-Jun (p-c-Jun (S63)); cSrc (p-cSrc (Y416)); and paxillin (p-paxillin (Y118)).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" refers to a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

III. Description of the Embodiments

The present invention provides antibody-based arrays for detecting the activation state and/or total amount of a plurality of signal transduction molecules in rare circulating cells and methods of use thereof for facilitating cancer prognosis and diagnosis and the design of personalized, targeted therapies.

A. Antibody Arrays

In one aspect, the present invention provides an array having superior dynamic range comprising a plurality of dilution series of capture antibodies specific for one or more analytes in a cellular extract, wherein the capture antibodies are restrained on a solid support.

In some embodiments, the cellular extract comprises an extract of circulating cells of a solid tumor. The circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

In other embodiments, the patient sample comprises a whole blood, serum, plasma, urine, sputum, bronchial lavage fluid, tears, nipple aspirate, lymph, saliva, and/or fine needle aspirate sample. In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), and combinations thereof. The plasma or serum fraction usually contains, inter alia, nucleic acids (e.g., DNA, RNA) and proteins that are released by circulating cells of a solid tumor.

In some instances, the isolated circulating cells can be stimulated in vitro with one or more growth factors before, during, and/or after incubation with one or more anticancer drugs of interest. Stimulatory growth factors include, but are not limited to, epidermal growth factor (EGF), heregulin (HRG), TGF-α, PlGF, angiopoietin (Ang), NRG1, PGF, TNF-α, VEGF, PDGF, IGF, FGF, HGF, cytokines, and the like. In other instances, the isolated circulating cells can be lysed, e.g., following growth factor stimulation and/or anticancer drug treatment, to produce the cellular extract (e.g., cell lysate) using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the cell lysate can be stored at −80° C. until use.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); and/or any other compound with the ability to reduce or abrogate the uncontrolled growth of aberrant cells such as cancerous cells. In some embodiments, the isolated circulating cells are treated with an anti-signaling agent and/or an anti-proliferative agent in combination with one or more chemotherapeutic agents.

Examples of anti-signaling agents suitable for use in the present invention include, without limitation, monoclonal antibodies such as trastuzumab (Herceptie®), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016), canertinib (CI 1033), semaxinib (SU5416), vatalanib (PTK787/ZK222584), sorafenib (BAY 43-9006; Nexavar®), imatinib mesylate (Gleevec®), and leflunomide (SU101); and combinations thereof.

Exemplary anti-proliferative agents include mTOR inhibitors such as sirolimus (rapamycin), temsirolimus (CCI-779), and everolimus (RAD001); Akt inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl)methyl)-4-piperidinyl)-2H-benz-imidazol-2-one, 10-(4'-(N-diethylamino)butyl)-2-chlorophenoxazine, 3-formylchromone thiosemicarbazone (Cu(II)Cl$_2$ complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125:1144-1145 (2003) and Kau et al., *Cancer Cell*, 4:463-476 (2003); and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

In preferred embodiments, the one or more analytes in the cellular extract comprise a plurality of signal transduction molecules. Examples of signal transduction molecules of interest are described above and include receptor tyrosine kinases, non-receptor tyrosine kinases, and/or tyrosine kinase signaling cascade components.

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto the array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

Figure 14:
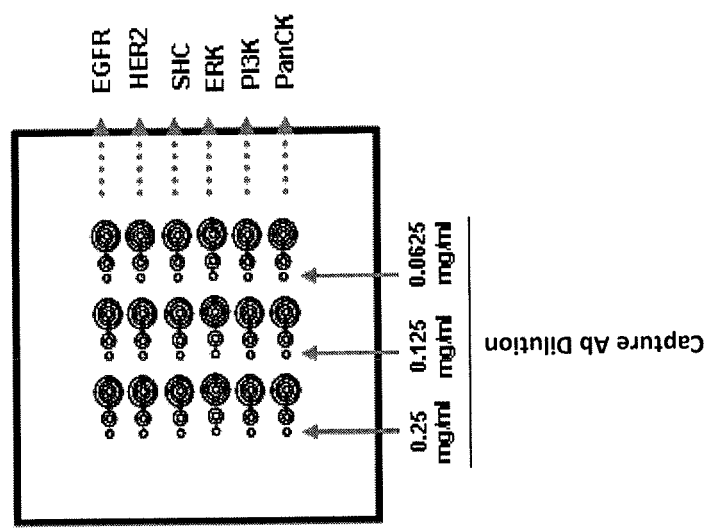
FIG. 14 shows an exemplary embodiment of the format of the addressable microarray using a dilution series of capture antibodies to determine the activation states of a plurality of signal transducer molecules.

As a non-limiting example, FIG. 14 illustrates an addressable microarray comprising a plurality of dilution series of capture antibodies to determine the activation states of EGFR, HER2, Shc, Erk, and PI3K in which the capture antibodies in each dilution series are directed to one of these analytes. Accordingly, the arrays of the present invention comprise a plurality of different capture antibodies in a series of descending concentrations (i.e., serial dilutions), wherein the capture antibodies are coupled to the surface of the solid support in different addressable locations.

One skilled in the art will appreciate that the array can be any configuration that allows discrete signals for each of the activated signal transduction molecules to be detected. For example, the array can be a line or a grid of distinct regions (e.g., dots or spots) on the support surface, where each region contains a different capture antibody or capture agent (i.e., to bind the capture tag present on the capture antibody). The array can be configured for use in methods where the activation states of a plurality of signal transduction molecules are detected in a single, multiplex assay. In various embodiments, the plurality comprises at least 2, 3, 4, 5, 6, 7, 8, 9, 10, 15, 20, 25, 30, 35, 40, 45, 50, or more signal transduction molecules.

B. Single Detection Assays

In another aspect, the assay for detecting the activation state of a particular analyte of interest in a cellular extract of tumor cells such as circulating cells of a solid tumor is a multiplex, high-throughput single detection (i.e., two-antibody) assay having superior dynamic range. As a non-limiting example, the two antibodies used in the assay can comprise: (1) a capture antibody specific for the analyte; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In a preferred aspect, the present invention provides a method for performing a multiplex, high-throughput immunoassay having superior dynamic range, the method comprising:
(a) incubating a cellular extract with a plurality of dilution series of capture antibodies specific for one or more analytes in the cellular extract to form a plurality of captured analytes, wherein the capture antibodies are restrained on a solid support;
(b) incubating the plurality of captured analytes with detection antibodies specific for the corresponding analytes to form a plurality of detectable captured analytes;
(c) incubating the plurality of detectable captured analytes with first and second members of a signal amplification pair to generate an amplified signal; and
(d) detecting an amplified signal generated from the first and second members of the signal amplification pair.

In some embodiments, the cellular extract comprises an extract of circulating cells of a solid tumor. The circulating cells are typically isolated from a patient sample using one or more separation methods known in the art including, for example, immunomagnetic separation, microfluidic separation, FACS, density gradient centrifugation, and depletion methods. Those of skill in the art will know of other methods suitable for the separation and/or isolation of circulating cells.

In other embodiments, the patient sample comprises a whole blood, serum, plasma, urine, sputum, bronchial lavage fluid, tears, nipple aspirate, lymph, saliva, and/or fine needle aspirate sample. In certain instances, the whole blood sample is separated into a plasma or serum fraction and a cellular fraction (i.e., cell pellet). The cellular fraction typically contains red blood cells, white blood cells, and/or circulating cells of a solid tumor such as CTCs, CECs, CEPCs, and/or CSCs. The plasma or serum fraction usually contains, inter alia, nucleic acids (e.g., DNA, RNA) and proteins that are released by circulating cells of a solid tumor.

In some instances, the isolated circulating cells can be stimulated in vitro with one or more growth factors before, during, and/or after incubation with one or more anticancer drugs of interest. Stimulatory growth factors are described above. In other instances, the isolated circulating cells can be lysed, e.g., following growth factor stimulation and/or anticancer drug treatment, to produce the cellular extract (e.g., cell lysate) using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the cell lysate can be stored at −80° C. until use.

In certain embodiments, the anticancer drug comprises an anti-signaling agent (e.g., monoclonal antibody, tyrosine kinase inhibitor, etc.), an anti-proliferative agent, a chemotherapeutic agent, and/or any other compound with the ability to reduce or abrogate the uncontrolled growth of aberrant cells such as cancerous cells. Examples of specific anticancer drugs which fall into these general classes of therapeutic agents are provided above.

In preferred embodiments, the one or more analytes in the cellular extract comprise a plurality of signal transduction molecules. Examples of signal transduction molecules of interest are described above and include, without limitation, receptor tyrosine kinases, non-receptor tyrosine kinases, and/or tyrosine kinase signaling cascade components.

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto the array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, PVDF, etc.), fiber bundles, or any other suitable substrate. In a preferred embodiment, the capture antibodies are restrained on glass slides coated with a nitrocellulose polymer such as, for example, FAST® Slides (Whatman Inc.; Florham Park, N.J.).

In certain instances, the cellular extract is incubated with capture antibodies already restrained on a solid support. In certain other instances, the cellular extract is first incubated with capture antibodies in solution and then contacted with a solid support to immobilize the captured analytes, e.g., via capture tags present on the capture antibodies which interact with capture agents bound to the solid support.

In some embodiments, the detection antibodies are incubated with analytes that are bound to capture antibodies in solution or restrained on a solid support. In certain instances, the cellular extract comprising a plurality of analytes is first incubated with the detection antibodies in solution and then contacted with capture antibodies in solution or restrained on a solid support. In certain other instances, the cellular extract comprising a plurality of analytes is first incubated with capture antibodies and detection antibodies in solution and then contacted with a solid support to immobilize the antibody-analyte complexes, e.g., via capture tags present on the capture antibodies or detection antibodies which interact with capture agents bound to the solid support.

In certain instances, the detection antibodies comprise activation state-independent antibodies, which are useful for detecting the total amount of one or more of the analytes in the cellular extract. As a non-limiting example, activation state-independent antibodies can detect both phosphorylated and unphosphorylated forms of one or more signal transduction molecules. In certain other instances, the detection antibodies comprise activation state-dependent antibodies, which are useful for detecting the activation state of one or more of the analytes in the cellular extract. Preferably, activation state-dependent antibodies detect the phosphorylation, ubiquitination, and/or complexation state of one or more signal transduction molecules.

The capture antibodies and detection antibodies are typically selected to minimize competition between them with respect to analyte binding (i.e., both capture and detection antibodies can simultaneously bind their corresponding signal transduction molecules).

In a preferred embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

One skilled in the art will appreciate that binding partners other than antibodies can be used to immobilize and/or detect one or more analytes from a cellular extract in accordance with the single detection assays described herein. Non-limiting examples of such binding partners include ligands or receptors of the analyte, substrates of the analyte, binding domains (e.g., PTB, SH2, etc.), aptamers, and the like.

C. Proximity Dual Detection Assays

In yet another aspect, the assay for detecting the activation state of a particular analyte of interest in a cellular extract of tumor cells such as circulating cells of a solid tumor is a multiplex, high-throughput proximity (i.e., three-antibody) assay having superior dynamic range. As a non-limiting example, the three antibodies used in the proximity assay can comprise: (1) a capture antibody specific for the analyte; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, for example, the phosphorylation, ubiquitination, and/or complexation state of the analyte. The activation state-dependent antibody is generally capable of detecting both the activated and non-activated forms of the analyte.

In a preferred aspect, the present invention provides a method for performing a multiplex, high-throughput immunoassay having superior dynamic range, the method comprising:
(a) incubating a cellular extract with a plurality of dilution series of capture antibodies specific for one or more analytes in the cellular extract to form a plurality of captured analytes, wherein the capture antibodies are restrained on a solid support;
(b) incubating the plurality of captured analytes with detection antibodies specific for the corresponding analytes to form a plurality of detectable captured analytes, wherein the detection antibodies comprise:
(1) a plurality of activation state-independent antibodies labeled with a facilitating moiety, and
(2) a plurality of activation state-dependent antibodies labeled with a first member of a signal amplification pair,
wherein the facilitating moiety generates an oxidizing agent which channels to and reacts with the first member of the signal amplification pair;

(c) incubating the plurality of detectable captured analytes with a second member of the signal amplification pair to generate an amplified signal; and
(d) detecting the amplified signal generated from the first and second members of the signal amplification pair.

FIG. 1 illustrates an exemplary proximity assay in which an analyte is bound to a capture antibody and two detection antibodies (i.e., an activation state-independent antibody and an activation state-dependent antibody). The capture antibody 1 and the activation state-independent antibody 2 each bind the analyte 6 independent of its activation state. The activation state-dependent antibody 3 binds the analyte dependent of its activation state (e.g., the activation state-dependent antibody will only bind an activated form of the analyte having a phosphorylated residue). The activation state-independent antibody is labeled with a facilitating moiety (designated M1, 4) and the activation state-dependent antibody is labeled with a first member of a signal amplification pair (designated M2, 5). Binding of both detection antibodies to the analyte brings the facilitating moiety within sufficient proximity (depicted by the area inside the dotted line 7) to the first member of the signal amplification pair such that a signal generated by the facilitating moiety can channel to the first member of the signal amplification pair resulting in the generation of a detectable and/or amplifiable signal. Various methods for proximity channeling are known in the art and include, for example, FRET, time-resolved fluorescence-FRET, LOCI, etc. An advantage of proximity channeling, as used in the methods of the present invention, is that a single detectable signal is generated for only those analytes that have bound all three antibodies, resulting in increased assay specificity, lower background, and simplified detection.

In some embodiments, the cellular extract comprises an extract of circulating cells of a solid tumor. The circulating cells are typically isolated from a patient sample using one or more separation methods known in the art including, for example, immunomagnetic separation, microfluidic separation, FACS, density gradient centrifugation, and depletion methods.

In other embodiments, the patient sample comprises a whole blood, serum, plasma, urine, sputum, bronchial lavage fluid, tears, nipple aspirate, lymph, saliva, and/or fine needle aspirate sample. In certain instances, the whole blood sample is separated into a plasma or serum fraction and a cellular fraction (i.e., cell pellet). The cellular fraction typically contains red blood cells, white blood cells, and/or circulating cells of a solid tumor such as CTCs, CECs, CEPCs, and/or CSCs. The plasma or serum fraction usually contains, inter alia, nucleic acids (e.g., DNA, RNA) and proteins that are released by circulating cells of a solid tumor.

In some instances, the isolated circulating cells can be stimulated in vitro with one or more growth factors before, during, and/or after incubation with one or more anticancer drugs of interest. Stimulatory growth factors are described above. In other instances, the isolated circulating cells can be lysed, e.g., following growth factor stimulation and/or anticancer drug treatment, to produce the cellular extract (e.g., cell lysate) using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the cell lysate can be stored at −80° C. until use.

In certain embodiments, the anticancer drug comprises an anti-signaling agent (e.g., monoclonal antibody, tyrosine kinase inhibitor, etc.), an anti-proliferative agent, a chemotherapeutic agent, and/or any other compound with the ability to reduce or abrogate the uncontrolled growth of aberrant cells such as cancerous cells. Examples of specific anticancer drugs which fall into these general classes of therapeutic agents are provided above.

In preferred embodiments, the one or more analytes in the cellular extract comprise a plurality of signal transduction molecules. Examples of signal transduction molecules of interest are described above and include, without limitation, receptor tyrosine kinases, non-receptor tyrosine kinases, and/or tyrosine kinase signaling cascade components.

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto the array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, PVDF, etc.), fiber bundles, or any other suitable substrate. In a preferred embodiment, the capture antibodies are restrained on glass slides coated with a nitrocellulose polymer such as, for example, FAST® Slides (Whatman Inc.; Florham Park, N.J.).

In certain instances, the cellular extract is incubated with capture antibodies already restrained on a solid support. In certain other instances, the cellular extract is first incubated with capture antibodies in solution and then contacted with a solid support to immobilize the captured analytes, e.g., via capture tags present on the capture antibodies which interact with capture agents bound to the solid support.

In some embodiments, the detection antibodies are incubated with analytes that are bound to capture antibodies in solution or restrained on a solid support. In certain instances, the cellular extract comprising a plurality of analytes is first incubated with the detection antibodies in solution and then contacted with capture antibodies in solution or restrained on a solid support. In certain other instances, the cellular extract comprising a plurality of analytes is first incubated with capture antibodies and detection antibodies in solution and then contacted with a solid support to immobilize the antibody-analyte complexes, e.g., via capture tags present on the capture antibodies or detection antibodies which interact with capture agents bound to the solid support. Prior to the detecting step, the immobilized complexes can be washed to remove uncomplexed antibodies, the washed complexes can be sequentially released from the support surface, and proximity channeling for each of the analytes being assayed can be detected by a suitable method as described herein.

Figure 2:
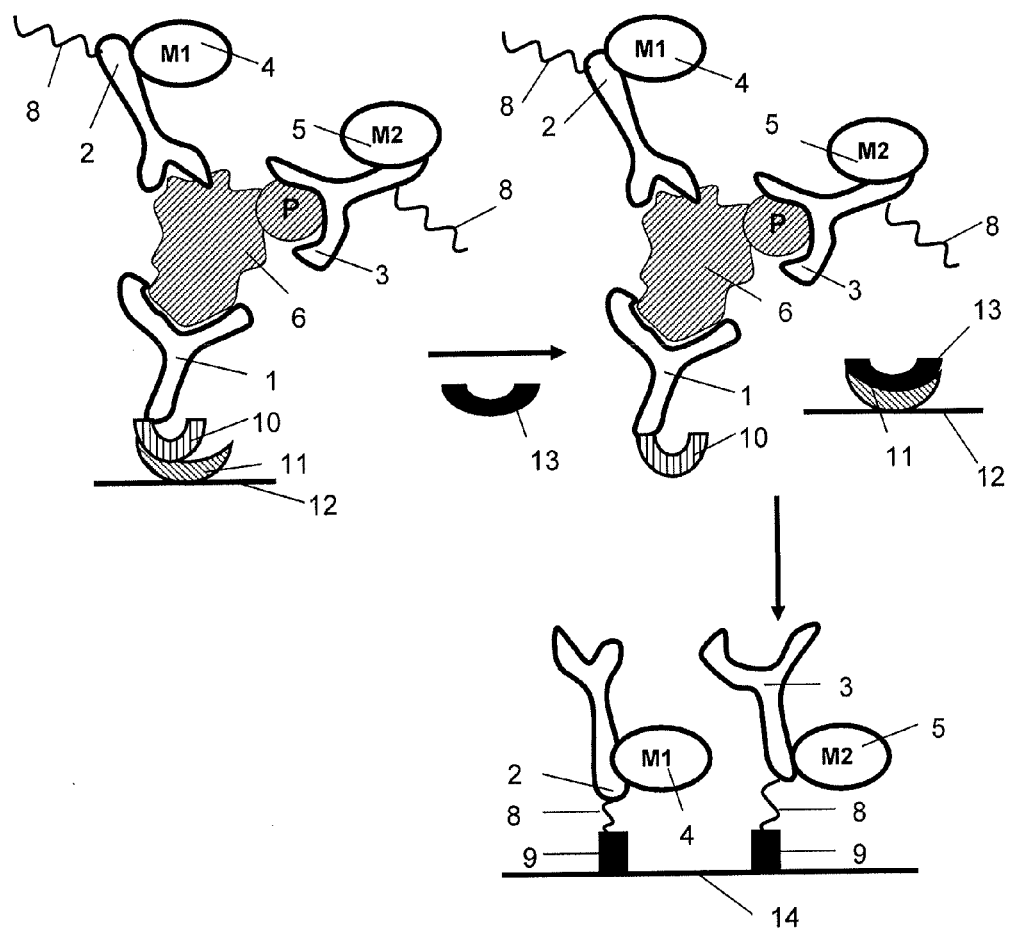
FIG. 2 shows an assay scheme where labeled antibodies that have specifically bound to an activated analyte are restrained on a solid support.

In embodiments where the support surface comprises capture agents restrained in an array, the incubating step can comprise contacting the cellular extract comprising a plurality of analytes in solution with the capture antibodies and detection antibodies, using an excess of all three antibodies to drive the reaction to completion. In one variation of the method, the resulting antibody-analyte complexes are attached to a solid phase and washed to remove unbound antibodies. Referring to FIG. 2, the capture antibody 1 can comprise a capture tag 10. The complexes are attached to a solid phase 12 via a capture agent 11 that is adhered to the solid phase and binds the capture tag, thereby immobilizing the complex. The immobilized complex is washed with a suitable buffer, and then released from the solid phase by the addition of a releasing agent 13. The releasing agent may function by any mechanism that results in the release of the washed complex. In one embodiment, the capture tag comprises a cleavable site that is recognized and cleaved by the releasing agent. In another embodiment, depicted in FIG. 2, the releasing agent competes with the capture tag for binding to the capture agent. For example, the capture agent may be a first oligonucleotide that hybridizes with a partially complementary oligonucleotide (i.e., the capture tag) attached to the capture antibody; and the releasing agent may be an oligonucleotide that is fully complementary to the capture agent, resulting in strand displacement and release of the washed complex from the solid phase. Other examples of suitable capture tags/capture agents/releasing agents that can be used include, but are not limited to, 2,4-dinitrophenol (DNP)/anti-DNP antibody/2,4-DNP lysine; T2/anti-T3 antibody/T3; ouabain/anti-digoxin antibody/digoxin; and dethiobiotin/streptavidin/biotin (see, e.g., Ishikawa et al., *J. Clin. Lab Anal.*, 12:98-107 (1998)).

After the washed complex is released from the solid phase, it is either: (1) contacted with a support surface comprising capture molecules restrained in an array that specifically bind capture tags on the capture antibody, or (2) dissociated, and the dissociated detection antibodies are contacted with a support surface comprising capture agents that specifically bind capture tags on the detection antibodies. FIG. 2 depicts the embodiment where the washed complex is dissociated and the dissociated detection antibodies are contacted with the support surface 14. The support surface comprises a plurality of capture molecules restrained in an "addressable" or "zip code" array. Each distinct region of the array comprises a unique capture agent 9 that specifically binds the capture tag 8 present on the activation state-independent detection antibody 2 or the activation state-dependent antibody 3, thereby restraining and organizing the tagged detection antibodies in the array. In a preferred embodiment, the capture agents and capture tags are oligonucleotides that specifically hybridize to each other. Addressable arrays comprising oligonucleotide capture molecules are well known in the art (see, e.g., Keramas et al., *Lab Chip*, 4:152-158 (2004); Delrio-Lafreniere et al., *Diag. Microbiol. Infect. Dis.*, 48:23-31 (2004)).

The presence of the detection antibodies at each distinct region of the array can be directly or indirectly detected with a moiety such as a facilitating moiety (designated M1, 4) or a first member of a signal amplification pair (designated M2, 5). Examples of moieties that can be directly detected include fluorophores, chromophores, colloidal gold, colored latex, etc. In one embodiment, the both moieties are independently selected fluorophores. Any pair of fluorophores that provide a distinguishable readout while in close proximity to each other can be used, such as, for example, Cy3/Cy5, Cy5/phycoerthrin, and the like. Alternatively, if an oligonucleotide addressable array is used, both moieties can be the same fluorophore delivered to different zip codes. Laser scanning confocal microscopy can be used to detect fluorophore moieties that are adhered on the array. In assays where the complexes are released from the array prior to detection, such as in strand displacement assays, suitable methods for detecting the fluorophore moieties include capillary flow confocal laser induced fluorescence, nano-HPLC, micro-capillary electrophoresis, etc.

In some embodiments, the activation state-independent antibodies further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well known in the art.

In certain instances, the activation state-independent antibodies are directly labeled with the facilitating moiety. The facilitating moiety can be coupled to the activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, the activation state-independent antibodies are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is no greater than 5° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-hybridization between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, the activation state-dependent antibodies are directly labeled with the first member of the signal amplification pair. The signal amplification pair member can be coupled to the activation state-dependent antibodies using methods well-known in the art. In certain other instances, the activation state-dependent antibodies are indirectly labeled with the first member of the signal amplification pair via binding between a first member of a binding pair conjugated to the activation state-dependent antibodies and a second member of the binding pair conjugated to the first member of the signal amplification pair. The binding pair members (e.g., biotin/streptavidin) can be coupled to the signal amplification pair member or to the activation state-dependent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

The capture antibodies, activation state-independent antibodies, and activation state-dependent antibodies are typically selected to minimize competition between them with respect to analyte binding (i.e., all antibodies can simultaneously bind their corresponding signal transduction molecules).

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

One skilled in the art will appreciate that binding partners other than antibodies can be used to immobilize and/or detect one or more analytes from a cellular extract in accordance with the proximity (i.e., three-antibody) assays described herein. Non-limiting examples of such binding partners include ligands or receptors of the analyte, substrates of the analyte, binding domains (e.g., PTB, SH2, etc.), aptamers, and the like.

D. Kits

In a further aspect, the present invention provides kits for performing the antibody-based array methods described above comprising: (a) a dilution series of a plurality of capture antibodies restrained on a solid support; and (b) a plurality of detection antibodies (e.g., activation state-independent antibodies and/or activation state-dependent antibodies). In some instances, the kits can further contain instructions for methods of using the kit to detect the activation states of a plurality of signal transduction molecules of circulating cells of a solid tumor. The kits may also contain any of the additional reagents described above with respect to performing the specific methods of the present invention such as, for example, first and second members of the signal amplification pair, tyramide signal amplification reagents, substrates for the facilitating moiety, wash buffers, capture/release reagents, etc.

IV. Construction of Antibody Arrays

In certain aspects, the present invention provides antibody-based arrays for detecting the activation state of a plurality of signal transduction molecules in a cellular extract of circulating cells of a solid tumor using a dilution series of capture antibodies restrained on a solid support. The arrays used in the assays of the present invention typically comprise a plurality of different capture antibodies at a range of capture antibody concentrations that are coupled to the surface of a solid support in different addressable locations.

The solid support can comprise any suitable substrate for immobilizing proteins. Examples of solid supports include, but are not limited to, glass (e.g., a glass slide), plastic, chips, pins, filters, beads (e.g., magnetic beads, polystyrene beads, etc.), paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies, the ability to bind capture antibodies with minimal denaturation, and the inability to bind other proteins. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating the arrays of the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating the antibody arrays of the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays of the present invention. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al, *Methods Mol. Biol.*, 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

V. Production of Antibodies

The generation and selection of antibodies not already commercially available for analyzing the activation state and/ or total amount of signal transduction molecules in rare circulating cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.,* 38:1192-99 (1990); Mostafavi et al., *Biomed. Pept. Proteins Nucleic Acids,* 1:255-60, (1995); and Fujiwara et al., *Chem. Pharm. Bull.,* 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic antibodies can also be prepared from genetic information by various procedures (see, e.g., *Antibody Engineering: A Practical Approach*, Borrebaeck, Ed., Oxford University Press, Oxford (1995); and Huse et al., *J. Immunol.,* 149:3914-3920 (1992)).

In addition, numerous publications have reported the use of phage display technology to produce and screen libraries of polypeptides for binding to a selected target antigen (see, e.g., Cwirla et al., *Proc. Natl. Acad. Sci. USA,* 87:6378-6382 (1990); Devlin et al., *Science,* 249:404-406 (1990); Scott et al., *Science,* 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057,098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N=C=NR$, wherein R and $R_1$ are different alkyl groups.

Animals are immunized against the polypeptide of interest or an immunogenic conjugate or derivative thereof by combining, e.g., 100 μg (for rabbits) or 5 μg (for mice) of the antigen or conjugate with 3 volumes of Freund's complete adjuvant and injecting the solution intradermally at multiple sites. One month later, the animals are boosted with about ⅕ to ⅒ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature,* 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA*, 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature*, 348:552-554 (1990); Clackson et al., *Nature*, 352:624-628 (1991); and Marks et al., *J. Mol. Biol.*, 222:581-597 (1991). The production of high affinity (nM range) human monoclonal antibodies by chain shuffling is described in Marks et al., *BioTechnology*, 10:779-783 (1992). The use of combinatorial infection and in vivo recombination as a strategy for constructing very large phage libraries is described in Waterhouse et al., *Nuc. Acids Res.*, 21:2265-2266 (1993). Thus, these techniques are viable alternatives to traditional monoclonal antibody hybridoma methods for the generation of monoclonal antibodies.

C. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature*, 321:522-525 (1986); Riechmann et al., *Nature*, 332:323-327 (1988); and Verhoeyen et al., *Science*, 239: 1534-1536 (1988). Accordingly, such "humanized" antibodies are chimeric antibodies (see, e.g., U.S. Pat. No. 4,816, 567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J. Immunol.*, 151: 2296 (1993); and Chothia et al., *J. Mol. Biol.*, 196:901 (1987)). Another method uses a particular FR derived from the consensus sequence of all human antibodies of a particular subgroup of light or heavy chains. The same FR may be used for several different humanized antibodies (see, e.g., Carter et al., *Proc. Natl. Acad. Sci. USA*, 89:4285 (1992); and Presta et al., *J. Immunol.*, 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

D. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immun.,* 7:33 (1993); and U.S. Pat. Nos. 5,591,669, 5,589,369, and 5,545,807.

Alternatively, phage display technology (see, e.g., McCafferty et al., *Nature,* 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.,* 3:564-571 (1993). Several sources of V-gene segments can be used for phage display. See, e.g., Clackson et al., *Nature,* 352:624-628 (1991). A repertoire of V genes from unimmunized human donors can be constructed and antibodies to a diverse array of antigens (including self-antigens) can be isolated essentially following the techniques described in Marks et al., *J. Mol. Biol.,* 222:581-597 (1991); Griffith et al., *EMBO J.,* 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

E. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.,* 24:107-117 (1992); and Brennan et al., *Science,* 229:81 (1985)). However, these fragments can now be produced directly using recombinant host cells. For example, the antibody fragments can be isolated from the antibody phage libraries discussed above. Alternatively, Fab'-SH fragments can be directly recovered from *E. coli* cells and chemically coupled to form F(ab')$_2$ fragments (see, e.g., Carter et al., *BioTechnology,* 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

F. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., *Meth. Enzymol.,* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., *Science*, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from *E. coli* and chemically coupled to form bispecific antibodies. For example, a fully humanized bispecific antibody F(ab')$_2$ molecule can be produced by the methods described in Shalaby et al., *J. Exp. Med.*, 175: 217-225 (1992). Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., *J. Immunol.*, 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

G. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

VI. Examples

The following examples are offered to illustrate, but not to limit, the claimed invention.

Example 1

Isolation, Stimulation, and Lysis of Circulating Cells

Circulating cells of a solid tumor comprise cells that have either metastasized or micrometastasized from a solid tumor and include circulating tumor cells (CTCs), cancer stem cells (CSCs), and/or cells that are migrating to the tumor (e.g., circulating endothelial progenitor cells (CEPCs), circulating endothelial cells (CECs), circulating pro-angiogenic myeloid cells, circulating dendritic cells, etc.). Patient samples containing circulating cells can be obtained from any accessible biological fluid (e.g., blood, urine, nipple aspirate, lymph, saliva, fine needle aspirate, etc.). The circulating cells can be isolated from a patient sample using one or more separation methods such as, for example, immunomagnetic separation (see, e.g., Racila et al., *Proc. Natl. Acad. Sci. USA,* 95:4589-4594 (1998); Bilkenroth et al., *Int. J. Cancer,* 92:577-582 (2001)), microfluidic separation (see, e.g., Mohamed et al., *IEEE Trans. Nanobiosci.,* 3:251-256 (2004); Lin et al., Abstract No. 5147, 97th AACR Annual Meeting, Washington, D.C. (2006)), FACS (see, e.g., Mancuso et al., *Blood,* 97:3658-3661 (2001)), density gradient centrifugation (see, e.g., Baker et al., *Clin. Cancer Res.,* 13:4865-4871 (2003)), and depletion methods (see, e.g., Meye et al., *Int. J. Oncol.,* 21:521-530 (2002)).

Manual Isolation of CTCs:

Immunomagnetic separation of CTCs—manual isolation followed by an activation assay:
1) Magnetic beads (Dynal M450; Dynal AS; Oslo, Norway) that have been previously conjugated to an anti-EpCAM monoclonal antibody (Kordia Life Sciences; Leiden, The Netherlands) are used.
2) Just prior to use, the pre-coated Dynabeads are washed once in an equal volume of PBS with BSA at 0.01%.
3) 25 µl of the pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with epithelial cells released from the punctured vein.
2) 1 ml of whole blood is diluted 1:3 with 0.9% NaCl prior to use.

Control preparation:
1) Cell line controls are made by spiking human cancer cell lines into HL-60 cells.
2) Cell line controls are used at a concentration of $2.5 \times 10^6$ cells/ml.

Manual Isolation of CECs and CEPCs:

As a non-limiting example, viable CECs and CEPCs can be isolated using the immunomagnetic isolation/enrichment technique described in Beereepoot et al., *Ann. Oncology,* 15:139-145 (2004). Briefly, peripheral blood is incubated with magnetic beads (Dynal M450 IgG$_1$) that have been previously conjugated to an anti-CD146 monoclonal antibody (Kordia Life Sciences). This antibody recognizes all lineages of endothelial cells, but not hematopoetic or epithelial cells, in peripheral blood (George et al., *J. Immunol. Meth.,* 139: 65-75 (1991)). Negative selection of hematopoetic and epithelial cells can be used prior to the positive selection with magnetic beads conjugated to appropriate antibodies (e.g., Dynal-CD45 beads for depleting leukocytes, Dynal-CD14 beads for depleting monocytes, Dynal-EpCAM for depleting epithelial cells (Invitrogen; Carlsbad, Calif.)). In this example, only positive selection is used.

Immunomagnetic separation of CECs and CEPCs—manual isolation followed by an activation assay:
1) Magnetic beads (Dynal M450) that have been previously conjugated to an anti-CD146 monoclonal antibody (Kordia Life Sciences) are used.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 1 ml of whole blood is diluted 1:3 with 0.9% NaCl prior to use.

Control preparation:
1) Cell line controls are made by spiking human umbilical vein endothelial cells (HUVEC) into HL-60 cells.
2) Cell line controls are used at a concentration of $2.5 \times 10^6$ cells/ml.

Manual Isolation of CEPCs (without CECs):

CEPCs are a circulating subtype of bone marrow-derived progenitor cells that have the capacity of differentiating into mature endothelial cells in response to various angiogenic growth factors. CEPCs may be isolated by selection with antibodies recognizing the surface marker CD34. CD133 is a surface marker that differentiates immature endothelial progenitor cells (EPCs) or primitive hematopoetic stem cells (HSCs) from CEPCs. Various isolation procedures of CEPCs from different sources have been described using adherence culture or magnetic microbeads. In this example, a protocol modified from that described in Asahara et al., *Science,* 275: 964-967 (1997) is used.

Immunomagnetic separation of CEPCs—manual isolation followed by an activation assay:
1) Magnetic beads (Dynal M450 CD34) are used. These beads are coated with a monoclonal antibody specific for the CD34 surface antigen.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Peripheral blood from human subjects is drawn in a siliconized tube containing 1 mg/ml EDTA. The first 3-5 ml is discarded to avoid contamination with endothelial cells released from the punctured vein.
2) 10 ml of blood is diluted 1:1 with a balanced salt solution.
3) 4 ml of diluted blood is layered onto 3 ml of Ficoll-Paque in 10 ml tubes.
4) Tubes are spun at 400×g for 30-40 min at 18-20° C.
5) The upper layer containing plasma and platelets is drawn off using a sterile Pasteur pipette, leaving the layer of mononuclear cells undisturbed at the interface.
6) The mononuclear cells are transferred to a sterile centrifuge tube using a sterile pipette.
7) 6 ml of balanced salt solution is added and the cells are gently resuspended.
8) The mixture is centrifuged at 60-100×g for 10 min at 18-20° C.
9) The supernatant is removed and the mononuclear cells from each tube are resuspended in 1 ml PBS.

Isolation of CTCs, CECs, and CEPCs Using the Veridex System:

Veridex (Warren, N.J.) has commercialized the CellSearch system, which consists of a CellPrep system, the CellSearch Epithelial Cell Kit, and the CellSpotter Analyzer. The CellPrep system is a semi-automated sample preparation system (Kagan et al., *J. Clin. Ligand Assay,* 25:104-110 (2002)). The CellSearch Epithelial Cell Kit consists of: ferrofluids coated with anti-EpCAM antibodies specific for epithelial cells; phycoerythrin-conjugated antibodies to cytokeratins 8, 18, and 19; an anti-CD45 antibody conjugated to allophycocyanin; DAPI dye; and buffers for washing, permeabilizing, and resuspending the cells. The protocol used in this example is also described in Allard et al., *Clin. Cancer Res.,* 10:6897-6904 (2004). The entire Veridex system can be used for CTC enumeration or, by removing the sample manually after isolation with the CellPrep system, can provide a method of isolation prior to analysis for pathway activation. The number of CTCs can be informative for algorithm development.

Veridex system—CTC enrichment followed by enumeration:
1) 7.5 ml of blood are mixed with 6 ml of buffer, centrifuged at 800×g for 10 minutes, and the placed on the CellPrep system.
2) After the instrument aspirates the supernatant, the instrument adds the ferrofluids.
3) The instrument performs the incubation and subsequent magnetic separation step.
4) Unbound cells and the remaining plasma are aspirated.
5) Staining reagents are added in conjunction with the permeabilization buffer for fluorescence staining.
6) After incubation by the system, the cells are again separated magnetically and resuspended in the MagNest Cell Presentation Device for analysis using the CellSpotter Analyzer.
7) The Device is placed on the CellSpotter Analyzer, a four-color semi-automated fluorescence microscope.
8) Images are captured that meet the Veridex defined criteria and are shown via a web-based browser for final manual selection.
9) Results of cell enumeration are expressed as the number of cells per 7.5 ml of blood.

Veridex system—CTC enrichment followed by an activation assay:
1) 7.5 ml of blood are mixed with 6 ml of buffer, centrifuged at 800×g for 10 minutes, and then placed on the CellPrep system.
2) After the instrument aspirates the supernatant, the instrument adds the ferrofluids.
3) The instrument performs the incubation and subsequent magnetic separation step.
4) Unbound cells and the remaining plasma are aspirated.
5) The sample is resuspended in 100 µl of stimulation buffer.

Veridex system—CEC and CEPC enrichment followed by an activation assay:
1) Veridex offers a CellTracks Endothelial Cell Kit utilizing capture of CECs and CEPCs with an anti-CD146 antibody. The CellTracks Endothelial Cell Kit is used in conjunction with Veridex's CellTracks AutoPrep System for blood sample preparation and the CellTracks Analyzer II to count and characterize CECs and CEPCs from whole blood. The protocol is the same as for the CellSearch Epithelial Cell Kit.

Sample preparation:
1) Peripheral blood from human subjects is drawn in the CellSave Preservative tube according to manufacturer's instructions. The first 3-5 ml is discarded to avoid contamination with epithelial or endothelial cells released from the punctured vein.

Manual Isolation of CSCs:

Evidence is building that tumors contain a small population of putative cancer stem cells with unique self-renewal and survival mechanisms (see, e.g., Sells, *Crit. Rev. Oncol. Hematol.,* 51:1-28 (2004); Reya et al., *Nature,* 414:105-111 (2001); Dontu et al., *Trends Endocrinol. Metal.,* 15:193-197 (2004); and Dick, *Nature,* 423:231-233 (2003)). Cancer stem cells (CSCs) may exist in a quiescent state for a long time, making them resistant to chemotherapeutic drugs which target dividing cells. This cancer-initiating population can be characterized for activation of self-renewal and survival pathways subject to targeted therapy for selective removal. Isolation procedures of CSCs have been described using adherence culture or magnetic microbeads. In this example, a protocol modified from that described in Cote et al., *Clin. Can. Res.,* 12:5615 (2006) is used.

Immunomagnetic CSC isolation—manual isolation followed by an activation assay:
1) Magnetic beads (Dynal AS; Oslo, Norway) are used. These beads are coated with a monoclonal antibody specific for either the CD34 or CD133 surface antigen.
2) Just prior to use, the pre-coated Dynabeads are washed once in an equal volume of PBS with BSA at 0.01%.
3) $1$-$10^7$ pre-coated Dynabeads are added to 3 ml of the sample.
4) The mixture is incubated for 60 minutes at 2-8° C. with gentle tilting and rotating.
5) The mixture is divided into 1 ml portions and each tube is placed in the magnetic separator (MPL-1 magnet) for at least 6 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Bone marrow specimens are obtained from early breast cancer patients following patient informed consent.
2) Processing the bone marrow aspirates is performed as described in Bauer et al., *Clin. Can. Res.,* 6:3552-3559 (2000)). The mononuclear cell fraction containing any disseminated tumor cells is enriched by Ficoll-Hypaque density gradient centrifugation using a Beckman GS-6 centrifuge at 4000×g for 35 minutes and washed twice with PBS.

Cell Stimulation and Lysis of Isolated CTCs:
Cell stimulation:
1) Growth factors TGF-α (100 nM), heregulin (100 nM), and/or IGF (100 nM) are added to the cells and incubated at 37° C. for 5 minutes.

Cell stimulation with drug treatment:
1) Sample is treated with Herceptin, Lapatanib, Tarceva, and/or Rapamycin analogs at therapeutically effective concentrations for 30 min. at 37° C.
2) Cells are then stimulated by adding growth factors TGF-α (100 nM), heregulin (100 nM), and/or IGF (100 nM) and incubated at 37° C. for 5 minutes.

Cell stimulation with drug treatment (feedback loop):
1) Sample is treated with Herceptin, Lapatanib, Tarceva, and/or Rapamycin analogs at therapeutically effective concentrations for 30 min. at 37° C.
2) Cells are then stimulated by TGF-α (100 nM), heregulin (100 nM), and/or IGF (100 nM) and incubated at 37° C. for 120 minutes.

Stimulated CTCs are lysed using the following protocol:
1) Fresh lysis buffer is freshly prepared by mixing the reagents set forth in Table 1.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

TABLE 1

Lysis Buffer recipe (10 ml)

| Reagents | Stock conc. | Final conc. | Volume |
|---|---|---|---|
| 10% Triton X-100 | 10 | 1 | 1.00 |
| 1M Tris, pH 7.5 | 1 | 0.05 | 0.05 |
| 1M NaF | 1 | 0.05 | 0.05 |
| 5M NaCl | 5 | 0.1 | 0.20 |
| 2M B-glycerolphosphate | 1 | 0.05 | 0.50 |
| 0.1M $Na_3VO_4$ | 0.1 | 0.001 | 0.10 |
| 1 mg/ml pepstatin | 1 | 0.10 | |
| Complete mini protease | | | 1 tablet |
| 0.5M EDTA | 0.5 | 0.005 | 0.10 |
| | | Total (ml) | 3.00 |
| | | Water (ml) | 7.00 |

Cell Stimulation and Lysis of Isolated CECs and/or CEPCs:
VEGF is thought to promote survival by activating anti-apoptotic pathways in both CEPCs (Larrivee et al., *J. Biol. Chem.*, 278:22006-22013 (2003)) and mature CECs, which have been sloughed off the vessel wall (Solovey et al., *Blood*, 93:3824-3830 (1999)). VEGF may also stimulate the proliferation of CEPCs or mature CECs, although mature CECs seem to have only a limited proliferative capacity compared with CEPCs (Lin et al., *J. Clin. Invest.*, 105:71-77 (2000)). For these reasons, CECs and/or CEPCs are activated by incubation with VEGF prior to lysis.

Cell stimulation:
1) The growth factors VEGF, FGF, PDGF, PIGF, and/or angiopoietin, each at 100 nM, are added to the cells and incubated at 37° C. for 5 minutes.

Cell stimulation with drug treatment:
1) Sample is treated with Avastin, Nexavar, Sutent, and/or Rapamycin analogs at therapeutically effective concentrations for 30 min. at 37° C.
2) Cells are then stimulated by adding growth factors VEGF, FGF, PDGF, PIGF, and/or angiopoietin, each at 100 nM, and incubated at 37° C. for 5 minutes.

Cell stimulation with drug treatment (feedback loop):
1) Sample is treated with Avastin, Nexavar, Sutent, and/or Rapamycin analogs at therapeutically effective concentrations for 30 min. at 37° C.
2) Cells are then stimulated by adding VEGF, FGF, PDGF, PIGF, and/or angiopoietin, each at 100 nM, and incubated at 37° C. for 120 minutes.

Isolated CECs and/or CEPC cells are lysed using the following protocol:
1) Fresh lysis buffer is freshly prepared by mixing the reagents set forth in Table 1.
2) After the final wash, cells are resuspended on ice in 1000 of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Cell Stimulation and Lysis of Isolated CSCs:
Stimulated cells:
1) Growth factors TGF-α (100 nM), heregulin (100 nM), and/or IGF (100 nM) are added to the cells and incubated at 37° C. for 5 minutes.

Stimulated cells with drug treatment:
1) Sample is treated with Herceptin, Lapatanib, Tarceva, and/or Rapamycin analogs at therapeutically effective concentrations for 30 min. at 37° C.
2) Cells are then stimulated by adding growth factors TGF-α (100 nM), heregulin (100 nM), and/or IGF (100 nM) and incubated at 37° C. for 5 minutes.

Stimulated cells with drug treatment (feedback loop):
1) Sample is treated with Herceptin, Lapatanib, Tarceva, and/or Rapamycin analogs at therapeutically effective concentrations for 30 min. at 37° C.
2) Cells are then stimulated by adding growth factors TGF-α (100 nM), heregulin (100 nM), and/or IGF (100 nM) and incubated at 37° C. for 120 minutes.

Isolated CSC cells are lysed using the following protocol:
1) Fresh lysis buffer is freshly prepared by mixing the reagents set forth in Table 1.
2) After the final wash, cells are re-suspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 2

Single Cell Detection Using a Single Detector Sandwich ELISA with Tyramide Signal Amplification This example illustrates a multiplex, high-throughput, single detector sandwich ELISA having superior dynamic range that is suitable for analyzing the activation states of signal transduction molecules in rare circulating cells:
1) A 96-well microtiter plate was coated with capture antibody overnight at 4° C.
2) The plate was blocked with 2% BSA/TBS-Tween for 1 hour the next day.

3) After washing with TBS-Tween, the cell lysate or recombinant protein was added at serial dilution and incubated for 2 hours at room temperature.
4) The plate was washed 4 times with TBS-Tween and then incubated with a biotin-labeled detection antibody for two hours at room temperature.
5) After incubation with the detection antibody, the plate was washed four times with TBS-Tween and then incubated with streptavidin-labeled horseradish peroxidase (SA-HRP) for 1 hour at room temperature to allow the SA-HRP to bind to the biotin-labeled detection antibody.
6) For signal amplification, biotin-tyramide was added at 5 μg/ml with 0.015% $H_2O_2$ and reacted for 15 minutes.
7) After washing six times with TBS-Tween, SA-HRP was added and incubated for 30 minutes.
8) After washing 6 times with TBS-Tween, the HRP substrate TMB was added and color was developed for 2-10 minutes in the dark. The reaction was stopped by adding of 0.5M $H_2SO_4$. The signal was read on a microplate reader at 450/570 nm.

FIGS. 3A-C show the detection of total EGFR in A431 cells using an ELISA comprising monoclonal antibodies against the extracellular domain of EGFR as the capture antibody and detection antibody. The sensitivity of the immunoassay was about 0.25 pg/well based on a recombinant extracellular domain of human EGFR. The calculated EGFR concentration was about 0.6 pg in each A431 cell.

Figures 4A, 4B:
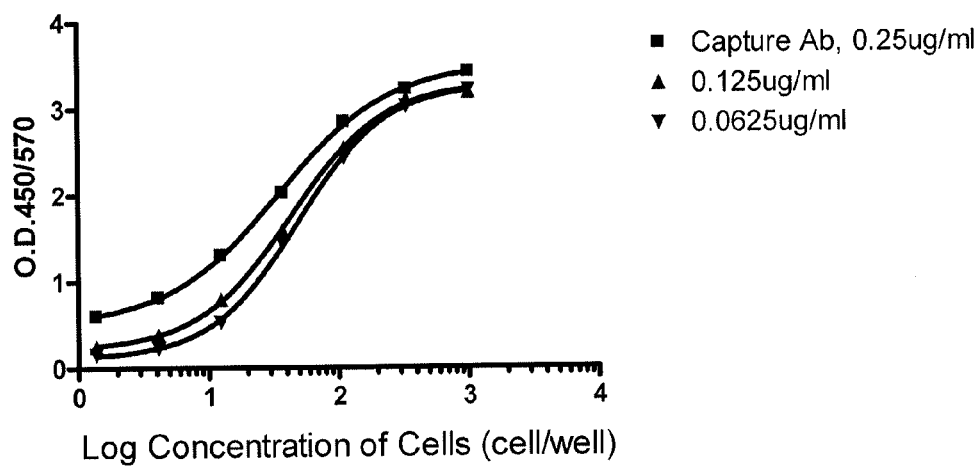
FIGS. 4A-B show the detection of phosphorylated EGFR in A431 cells using a monoclonal antibody against the extracellular domain of EGFR as the capture antibody and a biotin-labeled monoclonal antibody against phosphorylated EGFR as the detection antibody in an ELISA.

FIGS. 4A-B show the detection of phosphorylated EGFR in A431 cells using an ELISA comprising a monoclonal antibody against the extracellular domain of EGFR as the capture antibody and a biotin-labeled monoclonal antibody against phosphorylated EGFR as the detection antibody. Performing a 2-fold serial dilution of the capture antibody revealed that there was a 1.78-fold increase in signal over background (signal/noise ratio) at the one cell level when the capture antibody concentration was 0.0625 μg/ml.

Figures 5A, 5B:
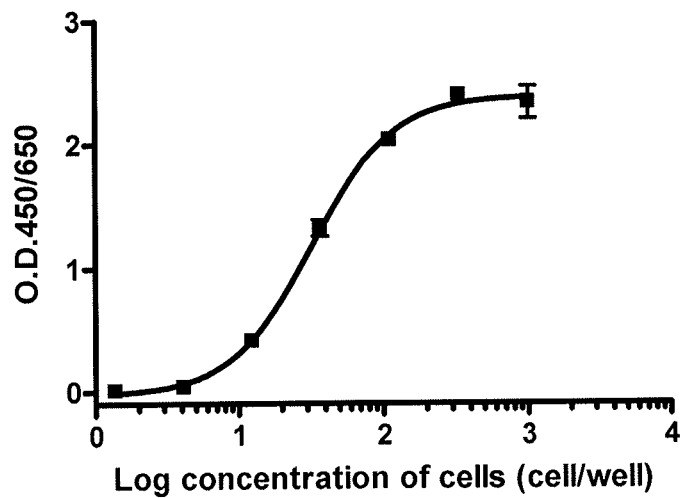
FIGS. 5A-B show the detection of total ErbB2 in SKBr3 cells using monoclonal antibodies against the extracellular domain of ErBb2 as the capture antibody and detection antibody in an ELISA.

FIGS. 5A-B show the detection of total ErbB2 in SKBr3 cells using an ELISA comprising monoclonal antibodies against the extracellular domain of ErBb2 as the capture antibody and detection antibody. The detection range of the immunoassay was between about 1,000 cells and about 1.37 cells. There was a 2.71-fold increase in signal over background (signal/noise ratio) at the 1.37 cell level when the capture antibody concentration was 1 μg/ml.

Figures 6A, 6B:
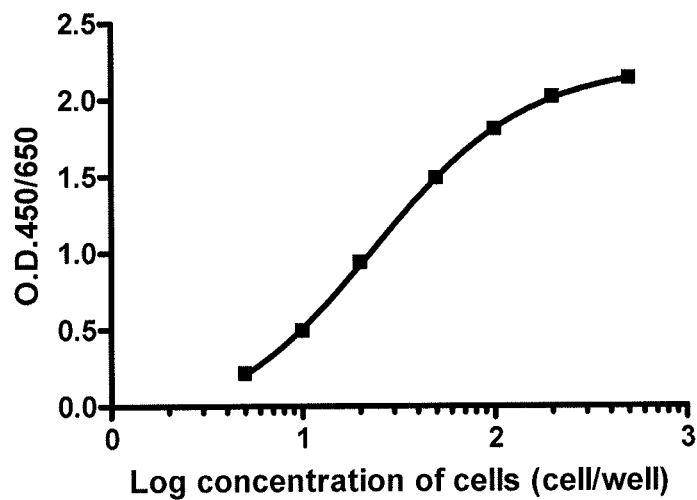
FIGS. 6A-B show the detection of phosphorylated ErBb2 in SKBr3 cells using a monoclonal antibody against the extracellular domain of ErbB2 as the capture antibody and a monoclonal antibody against phosphorylated ErbB2 as the detection antibody in an ELISA.

FIGS. 6A-B show the detection of phosphorylated ErBb2 in SKBr3 cells using an ELISA comprising a monoclonal antibody against the extracellular domain of ErbB2 as the capture antibody and a monoclonal antibody against phosphorylated ErBB2 as the detection antibody. The detection range of the immunoassay was between about 500 cells and about 5 cells. There was a 3.03-fold increase in signal over background (signal/noise ratio) at the 5 cell level when the capture antibody concentration was 1 μg/ml.

FIGS. 7A-C show the detection of total and phosphorylated Erk2 protein in SKBr3 cells using an ELISA comprising monoclonal antibodies against Erk2 as the capture antibody and detection antibody. There was a 3.25-fold increase in signal over background (signal/noise ratio) for total Erk2 at the 1.37 cell level. Likewise, there was a 3.17-fold increase in signal over background (signal/noise ratio) for phosphorylated Erk2 at the 1.37 cell level.

Example 3

Single Cell Detection Using a Single Detector Microarray ELISA with Tyramide Signal Amplification This example illustrates a multiplex, high-throughput, single detector microarray sandwich ELISA having superior dynamic range that is suitable for analyzing the activation states of signal transduction molecules in rare circulating cells:

1) Capture antibody was printed on a 16-pad FAST slide (Whatman Inc.; Florham Park, N.J.) with a 2-fold serial dilution.
2) After drying overnight, the slide was blocked with Whatman blocking buffer.
3) 80 μl of cell lysate was added onto each pad with a 10-fold serial dilution. The slide was incubated for two hours at room temperature.
4) After six washes with TBS-Tween, 80 μl of biotin-labeled detection antibody was incubated for two hours at room temperature.
5) After six washes, streptavidin-labeled horseradish peroxidase (SA-HRP) was added and incubated for 1 hour to allow the SA-HRP to bind to the biotin-labeled detection antibody.
6) For signal amplification, 80 μl of biotin-tyramide at 5 μg/ml was added and reacted for 15 minutes. The slide was washed six times with TBS-Tween, twice with 20% DMSO/TBS-Tween, and once with TBS.
7) 80 μl of SA-Alexa 555 was added and incubated for 30 minutes. The slide was then washed twice, dried for 5 minutes, and scanned on a microarray scanner (Perkin-Elmer, Inc.; Waltham, Mass.).

FIGS. 8A-C show the detection of total EGFR in A431 cells using a microarray ELISA comprising monoclonal antibodies against the extracellular domain of EGFR as the capture antibody and detection antibody. A capture antibody dilution curve experiment based upon cell numbers showed that the microarray ELISA format had a wide dynamic range to detect EGFR in about 1-10,000 cells with various concentrations of capture antibody in the dilution series. A cell titration curve experiment based upon the dilution series of capture antibody concentrations showed that EGFR could be detected from one cell. There was a 2.11-fold increase in signal over background (signal/noise ratio) at the one cell level when the capture antibody concentration was 0.0625 mg/ml.

FIGS. 9A-C show the detection of phosphorylated EGFR in A431 cells using a microarray ELISA comprising a monoclonal antibody against the extracellular domain of EGFR as the capture antibody and a monoclonal antibody against phosphorylated EGFR as the detection antibody. A capture antibody dilution curve experiment based upon cell numbers showed that the microarray ELISA format had a wide dynamic range to detect phosphorylated EGFR in about 1-10,000 cells with various concentrations of capture antibody in the dilution series. A cell titration curve experiment based upon the dilution series of capture antibody concentrations showed that phosphorylated EGFR could be detected from one cell. There was a 1.33-fold increase in signal over background (signal/noise ratio) at the one cell level when the capture antibody concentration was 0.125 mg/ml.

FIGS. 10A-C show the detection of total ErBb2 in SKBr3 cells using a microarray ELISA comprising monoclonal antibodies against the extracellular domain of ErBb2 as the capture antibody and detection antibody. A capture antibody dilution curve experiment based upon cell numbers showed that the microarray ELISA format had a wide dynamic range to detect ErBb2 in about 1-10,000 cells with various concentrations of capture antibody in the dilution series. A cell titration curve experiment based upon the dilution series of capture antibody concentrations showed that ErBb2 could be detected from one cell. There was a 15.27-fold increase in signal over background (signal/noise ratio) at the one cell level when the capture antibody concentration was 0.125 mg/ml.

FIGS. 11A-C show the detection of phosphorylated ErBb2 in SKBr3 cells using a microarray ELISA comprising a monoclonal antibody against the extracellular domain of ErBb2 as the capture antibody and a monoclonal antibody against phosphorylated ErBb2 as the detection antibody. A capture antibody dilution curve experiment based upon cell numbers showed that the microarray ELISA format had a wide dynamic range to detect ErBb2 in about 1-10,000 cells with various concentrations of capture antibody in the dilution series. A cell titration curve experiment based upon the dilution series of capture antibody concentrations showed that phosphorylated ErBb2 could be detected from one cell. There was a 5.45-fold increase in signal over background (signal/noise ratio) at the one cell level when the capture antibody concentration was 0.125 mg/ml.

Example 4

Single Cell Detection Using a Proximity Dual Detector Microarray ELISA with Tyramide Signal Amplification This example illustrates a multiplex, high-throughput, proximity dual detector microarray sandwich ELISA having superior dynamic range that is suitable for analyzing the activation states of signal transduction molecules in rare circulating cells:
1) Capture antibody was printed on a 16-pad FAST slide (Whatman Inc.) with a serial dilution of from 1 mg/ml to 0.004 mg/ml.
2) After drying overnight, the slide was blocked with Whatman blocking buffer.
3) 80 µl of A431 cell lysate was added onto each pad with a 10-fold serial dilution. The slide was incubated for two hours at room temperature.
4) After six washes with TBS-Tween, 80 µl of detection antibodies for the proximity assay diluted in TBS-Tween/2% BSA/1% FBS was added to the slides. The detection antibodies used were: (1) an anti-EGFR monoclonal antibody that was directly conjugated to glucose oxidase (GO); and (2) a monoclonal antibody recognizing phosphorylated EGFR that was directly conjugated to horseradish peroxidase (HRP). The incubation was for 2 hours at room temperature.
5) Alternatively, the detection step utilized a biotin-conjugate of the monoclonal antibody recognizing phosphorylated EGFR. In these instances, after six washes an additional sequential step of incubation with streptavidin-HRP for 1 hour was included.
6) Alternatively, the detection step utilized an oligonucleotide-mediated glucose oxidase (GO) conjugate of the anti-EGFR antibody. Either the directly conjugated or the biotin-steptavidin (SA) linked conjugate of HRP to the phosphorylated EGFR antibody was used.
6) For signal amplification, 80 µl of biotin-tyramide at 5 µg/ml was added and reacted for 15 min. The slide was washed six times with TBS-Tween, twice with 20% DMSO/TBS-Tween, and once with TBS.
7) 80 µl of SA-Alexa 555 was added and incubated for 30 min. The slide was then washed twice, dried for 5 minutes, and scanned on a microarray scanner (PerkinElmer, Inc.).

Figure 12:
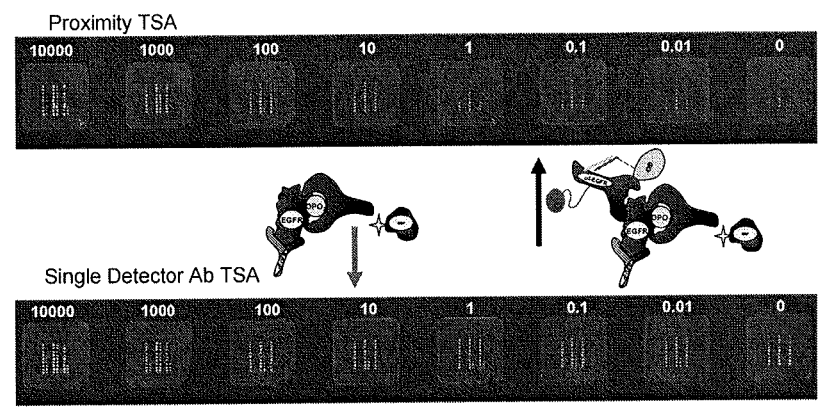
FIG. 12 shows a comparison of the sensitivity of the proximity dual detector microarray ELISA versus the single detector microarray ELISA. A431 cells were diluted from 10,000 to 0.01 cells. Capture antibodies were serially diluted from 1 mg/ml to 0.004 mg/ml.

FIG. 12 shows a comparison of the proximity dual detector microarray ELISA versus the single detector microarray ELISA. Table 2 shows the sensitivity of the proximity dual detector microarray ELISA versus the single detector microarray ELISA. For each A431 cell concentration, the signal over background (signal/noise ratio) for the proximity and single detector formats is shown. As illustrated in Table 2, the proximity dual detector microarray ELISA further increased sensitivity by about 3-fold at the one cell level.

TABLE 2

| Cell No. | Signal | Specific Signal | Proximity Format (S/N Ratio) | Single Detector Format (S/N Ratio) |
|---|---|---|---|---|
| 100 | 547 | 465 | 6.6 | 2.1 |
| 10 | 388 | 306 | 4.7 | 1.3 |
| 1 | 295 | 213 | 3.6 | 1.3 |
| 0 | 82 | | | |

Figure 13B:
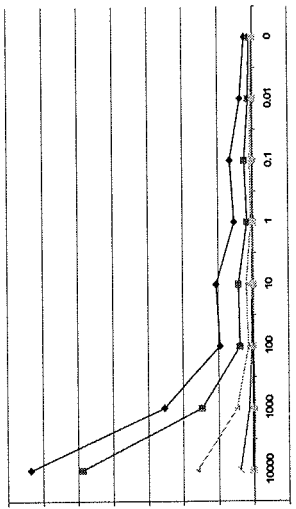
FIGS. 13A-B show the assay specificity for the single detector microarray ELISA versus the proximity dual detector microarray ELISA.
Figure 13A:
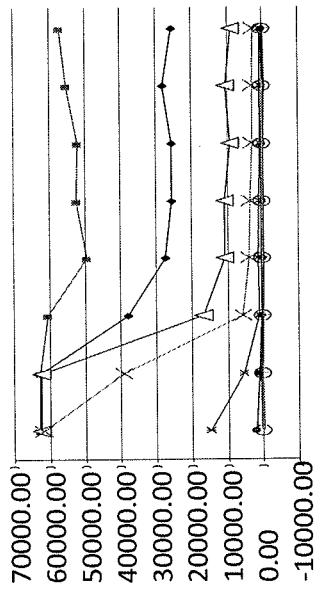

FIGS. 13A-B show the assay specificity for the single detector microarray ELISA versus the proximity dual detector microarray ELISA. Experiments which generated titration curves of phosphorylated EGFR at various capture antibody concentrations in the single detector format exhibited very high background due to the lack of specificity of the single detection antibody. In contrast, experiments which generated titration curves of phosphorylated EGFR at various capture antibody concentrations in the proximity dual detector format exhibited very low background due to the increased specificity obtained by detecting the proximity between two detection antibodies.

Example 5

Single Cell Detection of the Activation States of a Plurality of Signal Transducers Using Addressable Proximity Dual Detector Microarrays This example illustrates a multiplex, high-throughput, addressable proximity dual detector microarray assay having superior dynamic range that is suitable for analyzing the activation states of a plurality of signal transduction molecules in rare circulating cells:
1) Capture antibodies were printed on a 16-pad FAST slide (Whatman Inc.). The capture antibodies printed were EGFR, HER2, Erk, Shc, PI3K, and pan-cytokeratin. A 2-fold dilution series of each capture antibody (0.25 mg/ml, 0.125 mg/ml, and 0.0625 mg/ml) was used, and double and quadruple spots were made for each antibody dilution.
2) After drying overnight, the slide was blocked with Whatman blocking buffer.
3) 80 µl of cell lysate was added onto each pad with a 10-fold serial dilution. The slide was incubated for two hours at room temperature.
4) After six washes with TBS-Tween, 80 µl of detection antibodies for the proximity assay diluted in TBS-Tween/2% BSA/1% FBS was added to the slides. The detection antibodies used were: (1) an anti-EGFR monoclonal antibody that was directly conjugated to glucose oxidase (GO); and (2) a monoclonal antibody recognizing phosphorylated EGFR that was directly conjugated to HRP. The incubation was for 2 hours at room temperature.
5) Alternatively, the detection step utilized a biotin-conjugate of the monoclonal antibody recognizing phosphorylated EGFR. In these instances, after six washes an additional sequential step of incubation with streptavidin-HRP for 1 hour was included.
6) Alternatively, the detection step utilized an oligonucleotide-mediated glucose oxidase conjugate of the anti-EGFR antibody. Either the directly conjugated or biotin-steptavidin (SA) linked conjugate of HRP to the phosphorylated EGFR antibody was used.
7) To detect total HER2 and phosphorylated protein, steps 4), 5), or 6) were performed using a monoclonal antibody recognizing HER2 in place of the monoclonal antibody recognizing EGFR.
8) For signal amplification, 80 µl of biotin-tyramide at 5 µg/ml was added and reacted for 15 min. The slide was washed six times with TBS-Tween, twice with 20% DMSO/TBS-Tween, and once with TBS.
9) 80 µl of SA-Alexa 555 was added and incubated for 30 min. The slide was then washed twice, dried for 5 minutes, and scanned on a microarray scanner (Perkin-Elmer, Inc.).

FIG. 14 shows an exemplary embodiment of the format of the addressable microarray. Five targets are addressable via specific capture antibodies (e.g., EGFR, HER2, Shc, Erk, and PI3K). Phosphorylated complexes of Shc, Erk, or PI3K with either EGFR or HER2 can be detected on this array using the proximity dual detector format. Pan-cytokeratin (PanCK) serves as a control to normalize for the number of epithelial cells.

Figure 15:
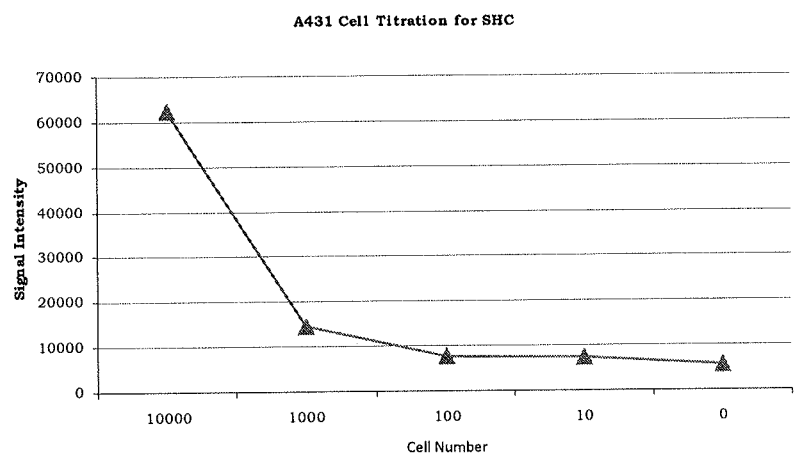
FIG. 15 shows the detection of phosphorylated Shc levels in a titration analysis of stimulated A431 cells. The addressable array simultaneously provided information on EGFR and HER2 phosphorylation.

FIG. 15 shows the detection of phosphorylated Shc levels in a titration analysis of stimulated A431 cells. The addressable array simultaneously provided information on EGFR and HER2 phosphorylation.

Example 6

Dynamic Range Extension of Proximity Dual Detector Microarrays

This example illustrates that the dynamic range for analyzing the activation states of signal transduction molecules in rare circulating cells can be enhanced by performing a dilution series on the capture antibody in a multiplex, high-throughput, proximity dual detector microarray assay:
1) Capture antibody was printed on a 16-pad FAST slide (Whatman Inc.). Each capture antibody was serially diluted 2-fold for a total of nine concentrations (1 mg/ml starting; 0.004 mg/ml ending).
2) After drying overnight, the slide was blocked with Whatman blocking buffer.
3) 80 µl of cell lysate was added onto each pad with a 10-fold serial dilution. The slide was incubated for two hours at room temperature.
4) After six washes with TBS-Tween, 80 µl of detection antibodies for the proximity assay diluted in TBS-Tween/2% BSA/1% FBS was added to the slides. The detection antibodies used were: (1) an anti-EGFR monoclonal antibody that was directly conjugated to glucose oxidase (GO); and (2) a monoclonal antibody recognizing phosphorylated EGFR that was directly conjugated to HRP. The incubation was for 2 hours at room temperature.
5) Alternatively, the detection step utilized a biotin-conjugate of the monoclonal antibody recognizing phosphorylated EGFR. In these instances, after six washes an additional sequential step of incubation with streptavidin-HRP for 1 hour was included.
6) Alternatively, the detection step utilized an oligonucleotide-mediated glucose oxidase conjugate of the anti-EGFR antibody. Either the directly conjugated or biotin-steptavidin (SA) linked conjugate of HRP to the phosphorylated EGFR antibody was used.
7) For signal amplification, 80 µl of biotin-tyramide at 5 µg/ml was added and reacted for 15 min. The slide was washed six times with TBS-Tween, twice with 20% DMSO/TBS-Tween, and once with TBS.
8) 80 µl of SA-Alexa 555 was added and incubated for 30 min. The slide was then washed twice, dried for 5 minutes, and scanned on a microarray scanner (Perkin-Elmer, Inc.).

Figure 16:
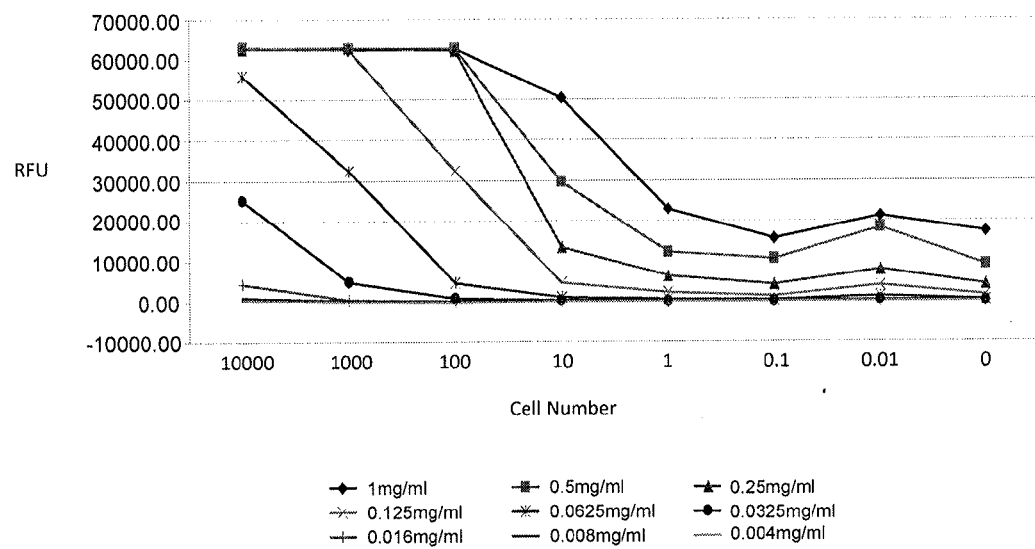
FIG. 16 shows the dilution curves of an anti-EGFR capture antibody. The dynamic range of this assay was greater than 5 logs. Each individual curve had a dynamic range of about 2 logs, but the dynamic range was significantly enhanced when the information from the 6 informative curves was combined.

FIG. 16 shows the dilution curves of an anti-EGFR capture antibody. Using addressable arrays, detection of phosphorylated and total EGFR was at the single cell level for stimulated A431 cells. The dynamic range of this assay was greater than 5 logs. Each individual curve had a dynamic range of about 2 logs, but the dynamic range was significantly enhanced when the information from the 6 informative curves was combined.

Example 7

Oligonucleotide Conjugation to Antibodies

This example illustrates a conjugation and quality control procedure for generating oligonucleotide-conjugated antibodies or enzymes.

Conjugation:
1) 72-mer oligonucleotide linkers were synthesized with a 5'-SH group and a 6-carbon spacer.
2) The lyophilized oligonucleotide linkers were dissolved in 20 mM Tris-HCl, pH 7.4. 125 nmoles of linkers were then treated with 0.5M TCEP-HCl (Pierce; Rockford, Ill.) at a final concentration of 50 mM at room temperature for 2 hrs. Tris, TCEP, and unconjugated linkers in the reaction mixture were eliminated using a desalting spin column.
3) The resulting deprotected oligonucleotide linkers were conjugated to the primary amines of target proteins (e.g., antibodies or enzymes) using a heterobifunctional cross-linker such as SMCC in a 100 µl reaction volume.
4) The reaction mix was incubated at room temperature for 2 hrs. The oligonucleotide-conjugated antibodies or enzymes were purified using gel filtration with a Sephacryl S-200 HR column (GE Healthcare; Piscataway, N.J.).

Conjugate Qualification:
1) After glucose oxidase (GO) molecules were conjugated to a first oligonucleotide linker, three fractions of the resulting GO-oligonucleotides were collected after purification and were printed on nitrocellulose-coated slides in a 10-fold dilution series.
2) IgG was conjugated to Alexa 647 and a second oligonucleotide linker having a sequence complementary to the first oligonucleotide linker. The resulting Alexa 647-oligonucleotide-conjugated antibodies were applied onto the chip and hybridized in 1×PBS buffer for 1 hr at room temperature and washed several times.
3) The slides were dried and scanned with a microarray scanner to confirm nucleotide sequence-specific hybridization.
4) A glucose oxidase enzymatic assay confirmed that the conjugation process did not alter the function of the enzyme.

Figure 17A:
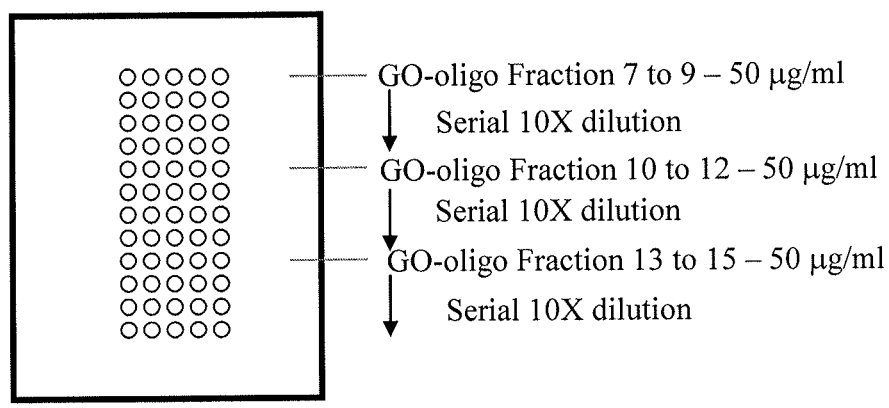
FIGS. 17A-B show a quality control procedure for the oligonucleotide conjugates of the present invention.
Figure 17B:
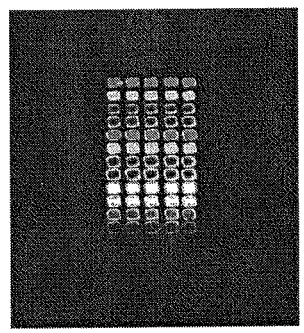

FIGS. 17A-B show that the Alexa 647-oligonucleotide-conjugated antibodies had the highest binding affinity for the GO-oligonucleotides in fractions 13-15.

Example 8

Figure 18:
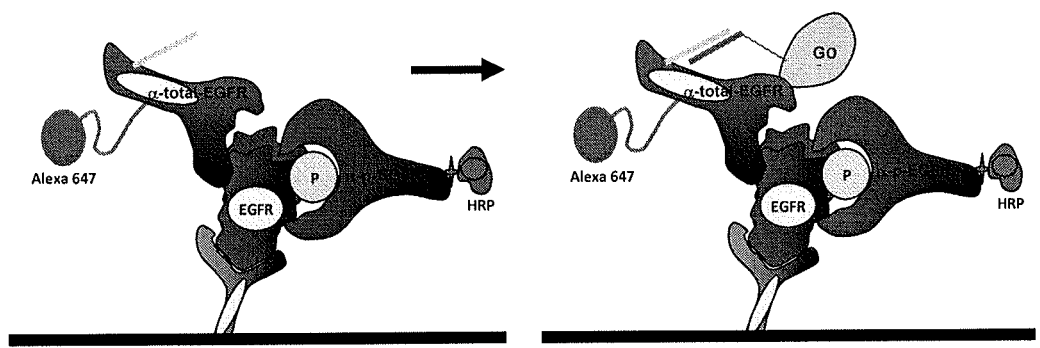
FIG. 18 shows the formation of a multiplexed phosphorylated EGFR complex comprising an Alexa 647-oligonucleotide-conjugated anti-EGFR antibody hybridized to a glucose oxidase (GO)-oligonucleotide, an HRP-conjugated anti-phosphorylated EGFR antibody, and an EGFR capture antibody restrained on a solid support.

Oligonucleotide-Conjugated Antibodies for Simultaneous Detection of Total and Phosphorylated EGFR This example illustrates a multiplex, high-throughput, microarray assay for analyzing the activation states of signal transduction molecules in rare circulating cells using the oligonucleotide conjugates described in Example 7:

1) Capture antibody was printed on a 16-pad FAST slide (Whatman Inc.).
2) After drying overnight, the slide was blocked with Whatman blocking buffer.
3) 80 µl of cell lysate was added onto each pad with a 10-fold serial dilution. The slide was incubated for two hours at room temperature.
4) After six washes with TBS-Tween, 80 µl of detection antibodies for the proximity assay diluted in TBS-Tween/2% BSA/1% FBS was added to the slides. The detection antibodies used were: (1) an anti-EGFR monoclonal antibody that was directly conjugated to Alexa 647 and an oligonucleotide linker, wherein the oligonucleotide linker comprises a sequence complementary to an oligonucleotide linker conjugated to glucose oxidase (GO); and (2) a monoclonal antibody recognizing phosphorylated EGFR that was directly conjugated to horseradish peroxidase (HRP). The Alexa 647-oligonucleotide-conjugated anti-EGFR antibody was contacted with the GO-oligonucleotide to form the complex shown in FIG. 18. Excess unbound reagents were removed by washing six times with TBS-Tween.
5) Glucose was then added to the reaction along with tyramide-Alexa 555.
6) Total EGFR levels were detected by direct binding of the Alexa 647-oligonucleotide-conjugated anti-EGFR antibody. Phosphorylated EGFR was detected by the proximity binding of the GO-oligonucleotide to the HRP-conjugated anti-p-EGFR antibody and visualized by tyramide signal amplification.
7) The slide was scanned with a laser specific for Alexa 647 and Alexa 555 on a microarray scanner (Perkin-Elmer, Inc.).

Figure 19A:
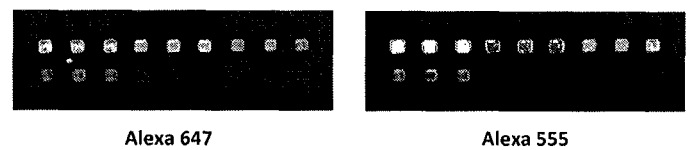
FIGS. 19A-B show the simultaneous detection of total EGFR and phosphorylated EGFR.
Figure 19B:
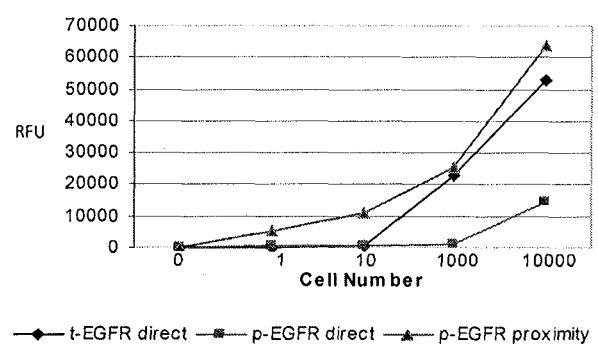

FIGS. 19A-B show the simultaneous detection of total EGFR and phosphorylated EGFR. Total EGFR (t-EGFR) was detected by a direct binding assay from as few as 10 cells and phosphorylated EGFR (p-EGFR) was detected from 1 cell. $10e^5$ p-EGFR molecules were detected with the proximity signal amplification method. The detection limit of p-EGFR was increased over 100-fold by using the proximity assay format.

Example 9

Detection of Circulating Tumor Cell (CTC) Signaling in Breast Cancer Patients Microarray fabrication and processing are adapted from methods described by Chan et al., *Nat. Med.*, 10:1390-1396 (2004). Antibodies (1 mg/ml) against the signal transducers EGFR, ErbB2, ErbB3, ErbB4, IGF-1R, Akt, Erk, p70S6K, Bad, Rsk, Mek, cSrc, cytokeratin, tubulin, β-actin, and anti-mouse antibody (Positive Control) (4/4 array) are transferred to a 384-well polypropylene plate (50 µl/well) using a contact printing robotic microarrayer (Bio-Rad Laboratories; Hercules, Calif.) fitted with solid spotting pins to spot antibodies onto FAST® Slides (Whatman Inc.; Florham Park, N.J.). Slides coated with 8 sectored pads are used. After printing, the slides are blocked with a 3% casein solution. Slides are stored at least overnight under dry conditions before use.

Patient selection criteria, sample preparation methods, and study design are adapted from published studies evaluating circulating tumor cells in women with suspected breast cancer (see, e.g., Wulfing et al., *Clin. Cancer Res.*, 12:1715-1720 (2006); and Reinholz et al., *Clin. Cancer Res.*, 11:3722-3732 (2005)). Women with a breast abnormality detected on imaging and who are to undergo a breast biopsy are approached for this study. At least forty-two patients who are diagnosed with primary breast cancer are included. At least thirty-five patients have no sign of overt metastasis at the time of primary diagnosis. At least seven patients have distant metastases at diagnosis and are considered a positive reference group. None of the patients have a history of previous cancer. Age and treatment information (e.g., surgical therapy, chemotherapy, radiotherapy, endocrine therapy, etc.) is collected for each patient. Approximately 20 ml of blood is collected from each patient and all blood samples are assigned a unique identification number. All assays are done with the investigators blinded to the results of the biopsy.

Peripheral blood (18 ml) is added to an Accuspin Histopaque-1077 system (Sigma Aldrich; St. Louis, Mo.) and centrifuged at 1,500 rpm for 10 minutes in a Beckman CS-6R tabletop centrifuge (Beckman Instruments; Palo Alto, Calif.). The mononuclear cell layer is removed, washed twice with PBS, and diluted to 1 ml with PBS/0.1% bovine serum albumin. The epithelial cells are enriched by immunomagnetic capture using antibodies against Ber-EP4 attached to magnetic beads using the Dynabeads Epithelial Enrich kit according to the manufacturer's instructions (Dynal AS; Oslo, Norway). The cells are mixed with 1-107 beads in a volume of 20 ml while rocking for 1 hour. The Ber-EP4 antibody recognizes two glycoproteins on the surface and in the cytoplasm of epithelial cells, except the superficial layers of squamous epithelial cells, hepatocytes, and parietal cells. The suspension is placed on a magnet for at least 6 minutes and the supernatant is carefully removed. The cells attached to the magnetic beads are washed thrice with 1 ml PBS/0.1% bovine serum albumin. Growth factors TGF-α (100 nM), heregulin (100 nM), and IGF (100 nM) are added to the cells and incubated at 37° C. for 5 minutes. The cells are concentrated and lysed with the lysis binding buffer supplied with the kit. The lysed cell suspension (with beads attached) is stored at 80° C. until processing.

Assay Method 1:

Lysates (40 µl) are applied to the array, incubated overnight, and washed three times with wash buffer. HRP-labeled anti-phospho antibody (conjugated as described, e.g., in Kuhlmann, Immuno Enzyme Techniques, Verlag Chemie, Weinheim, pp 1-162 (1984)) against each of the signal transducers and anti-total antibody (i.e., activation state-independent) labeled with glucose oxidase (conjugated as described in Kuhlmann, supra) are added to the array, incubated for 2 hours, and washed three times with wash buffer. Tyramide reagent (Molecular Probes) and glucose are added and the reaction is developed for one hour and washed three times. The array is incubated with streptavidin-HRP for 30 minutes and washed and developed using enhanced luminol (Molecular Probes). Signal is detected using a CCD camera.

Assay Method 2:

Antibodies (1 mg/ml) against 2,4-dinitrophenol (DNP) are transferred to a 384-well polypropylene plate (5 µl/well) using a contact printing robotic microarrayer (Bio-Rad Laboratories; Hercules, Calif.) fitted with solid spotting pins to spot antibodies onto FAST® Slides (Whatman Inc.; Florham Park, N.J.). Slides coated with 8 sectored pads are used. After printing, the slides are blocked with a 3% casein solution. Slides are stored at least overnight under dry conditions before use.

The lysate (40 µl) is mixed with total DNP-labeled antibody against each of the above signal transducers, anti-phospho antibody labeled with Oligo and Alexa Fluor® 647, and anti-total antibody labeled with Oligo and Alexa Fluor® 647, added to the anti-DNP antibodies, incubated overnight, and washed three times with wash buffer. 2,4-dinitro lysine (Molecular Probes) is added to release the immune complexes from the anti-DNP antibodies. The released immune complexes are added to a zip-code array (see, e.g., Keramas et al., *Lab Chip,* 4:152-158 (2004); and Delrio-Lafreniere et al., *Diagn. Microbiol. Infect. Dis.,* 48:23-31 (2004)) and incubated overnight. The array is washed three times and the processed slides are scanned using a GenePix 4000A microarray scanner (Axon Scanner) at 10 micron resolution.

Example 10

Detection of Circulating Endothelial Cell (CEC) and Circulating Endothelial Precursor Cell (CEP) Signaling in Breast Cancer Patients The same patient samples, sample preparation, and assay methods described in Example 9 are used, except that CEC and CEP cells are enriched by immunomagnetic capture using the monoclonal antibody P1H12 or CD146, attached to magnetic Dynabeads. A microarray is fabricated and processed using the methods described in Example 9, except that the arrayed antibodies are specific for the following analytes: VEGFR1, VEGFR2, VEGFR3, TIE1, TIE2, PDGFR-α, PDGFR-β, FGFR1, FGFR2, Akt, Erk, p70S6K, Rsk, cSrc, and β-actin. The assay methods described in Example 9 are used to detect CEC and CEP signaling.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An assay for performing a multiplex, high-throughput immunoassay having superior dynamic range, the assay comprising:
   (a) incubating a cellular extract with a plurality of dilution series of capture antibodies specific for one or more analytes in the cellular extract to form a plurality of captured analytes, wherein the capture antibodies are restrained on a solid support;
   (b) incubating the plurality of captured analytes with detection antibodies specific for the corresponding analytes to form a plurality of detectable captured analytes, wherein the detection antibodies comprise:
   (1) a plurality of activation state-independent antibodies labeled with glucose oxidase, and
   (2) a plurality of activation state-dependent antibodies labeled with a first member of a signal amplification pair, wherein the first member of the signal amplification pair is a peroxidase,
   wherein glucose oxidase generates hydrogen peroxide ($H_2O_2$), which channels to and reacts with the first member of the signal amplification pair;
   (c) incubating the plurality of detectable captured analytes with a second member of the signal amplification pair to generate an amplified signal; and
   (d) detecting the amplified signal generated from the first and second members of the signal amplification pair.

2. The assay of claim 1, wherein the cellular extract comprises an extract of circulating cells of a solid tumor.

3. The assay of claim 2, wherein the cells are isolated from a patient sample by immunomagnetic separation.

4. The assay of claim 3, wherein the patient sample is selected from the group consisting of whole blood, serum, plasma, urine, sputum, bronchial lavage fluid, tears, nipple aspirate, lymph, saliva, fine needle aspirate, and combinations thereof.

5. The assay of claim 3, wherein the isolated cells are selected from the group consisting of circulating tumor cells, circulating endothelial cells, circulating endothelial progenitor cells, cancer stem cells, and combinations thereof.

6. The assay of claim 3, wherein the isolated cells are i) stimulated in vitro with growth factors; or ii) incubated with an anticancer drug selected from the group consisting of a monoclonal antibody, tyrosine kinase inhibitor, immunosuppressive agent, and combinations thereof, prior to growth factor stimulation; or iii) lysed following growth factor stimulation to produce the cellular extract.

7. The assay of claim 1, wherein the one or more analytes comprise a plurality of signal transduction molecules.

8. The assay of claim 1, wherein the solid support is selected from the group consisting of glass, plastic, chips, pins, filters, beads, paper, membrane, fiber bundles, and combinations thereof.

9. The assay of claim 1, wherein the activation state-independent antibodies further comprise a detectable moiety, wherein said detectable moiety is a fluorophore.

10. The assay of claim 9, wherein the amount of the detectable moiety is correlative to the amount of one or more of the analytes.

11. The assay of claim 1, wherein the activation state-independent antibodies are directly labeled with glucose oxidase.

12. The assay of claim 1, wherein the activation state-independent antibodies are labeled with glucose oxidase via hybridization between an oligonucleotide conjugated to the activation state-independent antibodies and a complementary oligonucleotide conjugated to glucose oxidase.

13. The assay of claim 1, wherein the activation state-dependent antibodies are directly labeled with the first member of the signal amplification pair.

14. The assay of claim 1, wherein the activation state-dependent antibodies are labeled with the first member of the signal amplification pair via binding between a first member of a binding pair and a second member of the binding pair, wherein the first member of a binding pair is biotin conjugated to the activation state-dependent antibodies and a second member of the binding pair, wherein the second member of a binding pair is streptavidin conjugated to the first member of the signal amplification pair.

15. The assay of claim 1, wherein the peroxidase is horseradish peroxidase (HRP).

16. The assay of claim 14, wherein the second member of the signal amplification pair is a tyramide reagent, which is biotin-tyramide.

17. The assay of claim 16, wherein the amplified signal is generated by peroxidase oxidization of the biotin-tyramide to produce an activated tyramide.

18. The assay of claim 17, wherein the activated tyramide is directly detected.

19. The assay of claim 17, wherein the activated tyramide is detected upon the addition of a signal-detecting reagent, which is a streptavidin-labeled fluorophore.

20. The assay of claim 19, wherein the signal-detecting reagent is a combination of a streptavidin-labeled peroxidase and a chromogenic reagent, which is 3,3',5,5'-tetramethyl-benzidine (TMB).

\* \* \* \* \*